(12) United States Patent
Stocker

(10) Patent No.: US 11,220,530 B2
(45) Date of Patent: Jan. 11, 2022

(54) NANOSPHERES OF SEC14-LIKE PROTEINS AND COGNATE LIGANDS

(71) Applicant: UNIVERSITÄT BERN, Bern (CH)

(72) Inventor: Achim Stocker, Oberbottigen (CH)

(73) Assignee: UNIVERSITÄT BERN, Bern (CH)

( * ) Notice: Subject to any disclaimer, the term of this patent is extended or adjusted under 35 U.S.C. 154(b) by 0 days.

(21) Appl. No.: 16/072,454

(22) PCT Filed: Jan. 24, 2017

(86) PCT No.: PCT/EP2017/051409
§ 371 (c)(1),
(2) Date: Jul. 24, 2018

(87) PCT Pub. No.: WO2017/129555
PCT Pub. Date: Aug. 3, 2017

(65) Prior Publication Data
US 2019/0071475 A1    Mar. 7, 2019

(30) Foreign Application Priority Data

Jan. 25, 2016 (EP) ..................................... 16152579

(51) Int. Cl.
| | | |
|---|---|---|
| *C07K 14/47* | (2006.01) | |
| *B82Y 5/00* | (2011.01) | |
| *B82Y 40/00* | (2011.01) | |
| *A61K 47/50* | (2017.01) | |
| *A61P 25/14* | (2006.01) | |
| *A61P 3/02* | (2006.01) | |
| *A61P 21/00* | (2006.01) | |
| *A61P 19/02* | (2006.01) | |
| *A61P 29/00* | (2006.01) | |
| *A61K 9/14* | (2006.01) | |
| *A61K 9/51* | (2006.01) | |
| *A61K 38/17* | (2006.01) | |
| *A61K 38/00* | (2006.01) | |

(52) U.S. Cl.
CPC .............. *C07K 14/47* (2013.01); *A61K 9/146* (2013.01); *A61K 9/51* (2013.01); *A61K 38/1709* (2013.01); *A61K 47/50* (2017.08); *A61P 3/02* (2018.01); *A61P 19/02* (2018.01); *A61P 21/00* (2018.01); *A61P 25/14* (2018.01); *A61P 29/00* (2018.01); *B82Y 5/00* (2013.01); *B82Y 40/00* (2013.01); *A61K 38/00* (2013.01)

(58) Field of Classification Search
CPC .................. A61K 45/06; A61K 31/355; A61K 2039/6031; A61K 9/51; C12Q 2600/136; A61P 43/00; A61P 3/02; A61P 3/00; C12N 15/1089; C12N 15/1138; C07K 14/47; C07K 14/4702; G01N 2333/705; G01N 33/566; G01N 33/68
See application file for complete search history.

(56) References Cited

U.S. PATENT DOCUMENTS 6,268,170 B1    7/2001    Siddique et al.

OTHER PUBLICATIONS

Peltzer et al. Self-Assembly of α-Tocopherol Transfer Protein Nanoparticles: A Patchy Protein Model. J Phys Chem B. Jul. 19, 2018; 122(28):7066-7072. (Year: 2018).*
Panagabko et al. Ligand Specificity in the CRAL-TRIO Protein Family. Biochemistry 2003, 42, 6467-6474. (Year: 2003).*
NCBI P49638. https://www.ncbi.nlm.nih.gov/protein/P49638. 1[Sep. 5, 2020 10:48:59 PM] (Year: 2020).*
Meier et al. The Molecular Basis of Vitamin E Retention: Structure of Human α-Tocopherol Transfer Protein. J. Mol. Biol. (2003) 331, 725-734. (Year: 2003).*
Helbling et al., "Engineering Tocopherol Selectivity in α-TTP: A Combined *In Vitro/In Silico* Study," PLoS One 7(11):e49195 (2012).
Min et al., "Crystal structure of human α-tocopherol transfer protein bound to its ligand: Implications for ataxia with vitamin E deficiency," PNAS 100(25):14713-14718 (2003).
Mitragotri et al., "Overcoming the challenges in administering biopharmaceuticals: formulation and delivery strategies," Nature Reviews Drug Discovery 13(9):655-672 (2014).
Ouahchi et al., "Ataxia with isolated vitamin E deficiency is caused by mutations in the α-tocopherol transfer protein," Nature Genetics 9:141-145 (1995).
Yuan et al., "Dimeric Sfh3 has structural changes in its binding pocket that are associated with a dimer-monomer state transformation induced by substrate binding," Acta Crystallographica Section D: Biological Crystallography D69:313-323 (2013).
International Search Report for PCT/EP2017/051409, dated Mar. 30, 2017.

* cited by examiner

*Primary Examiner* — Soren Harward
*Assistant Examiner* — Jia-Hai Lee
(74) *Attorney, Agent, or Firm* — Medler Ferro Woodhouse & Mills PLLC

(57)    ABSTRACT

The present invention relates to a nanosphere comprising an equal number of a human SEC14-like protein and a cognate ligand of said SEC14-like protein as well as to methods of producing the same and uses of said nanospheres.

19 Claims, 14 Drawing Sheets

Specification includes a Sequence Listing.

| Interface | Energy [kcal mol$^{-1}$] | Surface [Å$^2$] |
|---|---|---|
| 3-fold symmetry axis | -9.76 ± 0.32 | 438.00 |
| Residue 1 | Residue 2 | Interaction |
| R151 | E275, Q278 | Salt Bridge |
| R57 | Q278 | Salt Bridge |
| R57 | E275 | Hydrogen Bond |
| F61 | Y74, I277, S276 | vdW |
| L56 | Y74 | vdW |
| D64 | K71 | Salt Bridge |
| L63 | K71, L70, W67 | vdW |
| W67 | W67, D64, L63 | vdW |

SEQ ID NO:3

MAEARSQPSAGPQLNALPDHSPLLQPGLAALRRRAREAGVPLAPLPLTDSFLLRFLRARD
FDLDLAWRLLKNYYKWRAECPEISADLHPRSIIGLLKAGYHGVLRSRDPTGSKVLIYRIA
HWDPKVFTAYDVFRVSLITSELIVQEVETQRNGIKAIFDLEGWQFSHAFQITPSVAKKIA
AVLTDSFPLKVRGIHLINEPVIFHAVFSMIKPFLTEKIKERIHMHGNNYKQSLLQHFPDI
LPLEYGGEEFSMEDICQEWTNFIMKSEDYLSSISESIQ

SEQ ID NO:4

MSEGVGTFRMVPEEEQELRAQLEQLTTKDHGPVFGPCSQLPRHTLQKAKDELNEREETRE
EAVRELQEMVQAQAASGEELAVAVAERVQEKDSGFFLRFIRARKFNVGRAYELLRGYVNF
RLQYPELFDSLSPEAVRCTIEAGYPGVLSSRDKYGRVVMLFNIENWQSQEITFDEILQAY
CFILEKLLENEETQINGFCIIENFKGFTMQQAASLRTSDLRKMVDMLQDSFPARFKAIHF
IHQPWYFTTTYNVVKPFLKSKLLERVFVHGDDLSGFYQEIDENILPSDFGGTLPKYDGKA
VAEQLFGPQAQAENTAF

SEQ ID NO:5

MGPVSLLPKYQKLNTWNGDLAKMTHLQAGLSPETIEKARLELNENPDVLHQDIQQVRDMI
ITRPDIGFLRTDDAFILRFLRARKFHQADAFRLLAQYFQYRQLNDMFKNFKADDPGIKR
ALIDGFPGVLENRDHYGRKILLLFAANWDQSRNSFTDILRAILLSLEVLIEDPELQINGF
ILIIDWSNFSFKQASKLTPSILKLAIEGLQDSFPARFGGVHFVNQPWYIHALYTLIKPFL
KDKTRKRIFLHGNNLNSLHQLIHPEFLPSEFGGTLPPYDMGTWARTLLGPDYSDENDYTH
TSYNAMHVKHTSSNLERECSPKLMKRSQSVVEAGTLKHEEKGENENTQPLLALD

SEQ ID NO:6

MTHLQAGLSPETIEKARLELNENPDTLHQDIQEVRDMVITRPDIGFLRTDDAFILRFLRA
RKFHHFEAFRLLAQYFEYRQQNLDMFKSFKATDPGIKQALKDGFPGGLANLDHYGRKILV
LFAANWDQSRYTLVDILRAILLSLEAMIEDPELQVNGFVLIIDWSNFTKQASKLTPSML
RLAIEGLQDSFPARFGGIHFVNQPWYIHALYTVIRPFLKEKTRKRIFLHGNNLNSLHQLI
HPEILPSEFGGMLPPYDMGTWARTLLDHEYDDDSEYNVDSYSMPVKEVEKELSPKSMKRS
QSVVDPTVLKRMDKNEEENMQPLLSLD

SEQ ID NO:7

MSEESDSLRTSPSVASLSENELPPPPEPPGYVCSLTEDLVTKAREELQEKPEWRLRDVQA
LRDMVRKEYPNLSTSLDDAFLLRFLRARKFDYDRALQLLVNYHSCRRSWPEVFNNLKPSA
LKDVLASGFLTVLPHTDPRGCHVVCIRPDRWIPSNYPITENIRAIYLTLEKLIQSEETQV
NGIVILADYKGVSLSKASHFGPFIAKKVIGILQDGFPIRIKAVHVVNEPRIFKGIFAIIK
PFLKEKIANRFFLHGSDLNSLHTNLPRSILPKEYGGTAGELDTATWNAVLLASEDDFVKE
FCQPVPACDSILGQTLLPEGLTSDAQCDDSLRAVKSQLYSCY

FIG. 9

NANOSPHERES OF SEC14-LIKE PROTEINS AND COGNATE LIGANDS

The present invention relates to a nanosphere comprising an equal number of a human SEC14-like protein and a cognate ligand of said SEC14-like protein as well as to methods of producing the same and uses of said nanospheres.

RELATED ART

The SEC14 gene product SEC14p was first identified in the yeast *Saccharomyces cerevisiae*, where it serves as transfer protein of phosphatidylinositol from the Golgi apparatus to the plasma membrane. The X-ray structure of the domain in SEC14 proteins reveals a characteristic alpha-beta-alpha sandwich with a hydrophobic pocket for lipid binding. Sec14p is essential for the biogenesis of secretory vesicles from the trans-Golgi network by integrating lipid signalling events with proteins involved in vesicle budding. Yeast homologs of SEC14p (SFH2, SFH3, SFH4, and SFH5) fulfil complementary functions by modulating PtdIns kinase and phospholipase D activities and by promoting phosphoinositide production (LLi, X., et al., Mol Biol Cell. 2000 11:1989-2005 and references cited therein).

In higher eukaryotes functional homologs of yeast SEC14p constitute the SEC14-like family of proteins with related functions (Peterman, T. K., et al., Plant Physiol. 2004 136: 3080-3094). Protein sequence analysis and classification by the InterPro integrated database (https://www.ebi.ac.uk/interpro/) predicts that all members of the SEC14-like family of proteins have in common a characteristic CRAL-TRIO (IPR001251) domain derived from the primary structure of CRALBP and the triple function TRIO protein. The CRAL-TRIO domain represents a structural scaffold for sequestering small lipophilic molecules (Panagabko C, et al., Biochemistry 2003 42:6467-6474 and references cited therein). The domain may either constitute all of a SEC14-like protein or only part of it. CRAL-TRIO-only proteins like SEC14p, CRALBP or α-TTP have been identified as cytosolic factors for the intermembrane transfer of phosphatidylinositol, 11-cis-retinal and of α-tocopherol (α-tol) respectively (Panagabko C, et al., Biochemistry 2003 42:6467-6474 and references cited therein). α-Tocopherol transfer protein (α-TTP) is a cytosolic 32 kDa protein that facilitates the transport of lipophilic vitamin E molecules through hydrophilic media and to be assimilated by the organism. It belongs to the SEC14-like protein family, known to be involved in lipid regulation (Panagabko C, et al., Biochemistry 2003 42:6467-6474; L. Aravind, et al., Curr. Biol. 1999 9:195-197 and references cited therein). The fold consists of five parallel 3-strands constituting the floor of the binding cavity, a variable number of alpha-helices and a mobile helical gate at the carboxy-terminal region that allows the lipophilic cognate ligand to access the binding pocket (Stocker A. Ann N Y Acad Sci. 2004 1031:44-59; Meier R, et al., J Mol Biol 2003 331: 725-734). α-TTP has been isolated in both rats and humans, and it is mainly expressed in the liver, but it is also present in the placenta and in the brain (Kaempf-Rotzoll, et al., Placenta 2003 24, 439-444 and references cited therein). α-TTP plays a key role in the regulation of vitamin E in hepatocytes and is essential to the health of the organism, as its poor expression or mutation is directly associated to occurrence of AVED genetic disease (Ouahchi K., et al., Nat. Genet. 1995 9:141-145).

In 1987, Cellular retinaldehyde-binding protein (CRALBP) was identified as high affinity binder with nanomolar affinities for 9-cis-retinal ($K_d$=53 nM), 11-cis-retinal ($K_d$=20 nM) and 11-cis-retinol (Kd=60 nM) (Saari J C, and Bredberg D L., J Biol Chem. 1987 262:7618-22). The same study showed that CRALBP does not bind to either 13-cis or all-trans-retinal. An additional function of CRALBP is given by its capability of protecting its cognate cis-cognate ligands from premature isomerization. CRALBP also increases the retinal flux of the visual cycle, the eye's biochemical regeneration pathway from all-trans-retinal to 11-cis-retinal. In this pathway CRALB stimulates the isomerase activity of RPE65 (P. D. Kiser, et al., 2015 Nature Chemical Biology 11:409-415) and facilitates binding of 11-cis-retinol into the RDH5 dehydrogenase (Gamble M V1, et al., J Lipid Res. 1999 40:2279-92). Finally it chaperones translocation of 11-cis-retinal from RDH5 through the cytoplasm out of the cell by unknown mechanisms. Characterization of gene mutations of human CRALBP could show that this protein is essential for efficient dark adaptation in rods and cones (M. S. Burstedt, et al., 2003 Vision Res. 43:2559-2571).

The SEC14-like Clavesins 1 and 2 are both expressed exclusively in neurons. These proteins are cytosolic but also bind to the endosome/lysosome compartment through their CRAL-TRIO domains by interacting with phosphatidylinositol 3,5-bisphosphate abundant in the endosomal membrane (Katoh Y, et al., J Biol Chem. 2009 284:27646-54). Clavesins are enriched on clathrin coated vesicles where they form a complex with clathrin heavy chain and adaptor protein-1, major coat components of clathrin coated vesicles. Isoform-specific knockdown of clavesins in neurons using lentiviral delivery of interfering RNA indicates a unique neuron-specific regulation of late endosome/lysosome morphology (Katoh Y, et al., J Biol Chem. 2009 284:27646-54).

SEC14-like proteins such as α-TTP and CRALBP bind specific natural cognate ligands with low nano-molar affinity. Such cognate ligands are sequestered from the plasma and selected to overcome the thermodynamic barrier impairing free diffusion of insoluble lipids (Cohn, W., Am J Clin Nutr 1999 69:156-157). CRALBP-mediated intracellular 11-cis-retinal transfer in the eye is essential for persistent vision (M. S. Burstedt, et al., 2003 Vision Res. 43:2559-2571). α-TTP is essential for vitamin E homeostasis in man by selectively retaining α-tocopherol, the vitamin E isomer with the highest antioxidant potency (Kono, N. and Arai, H. Traffic 2015 16: 19-34).

Numerous heritable diseases are linked to SEC14-like proteins. Defects in the human α-TTP gene product of TTPA are reported to cause phenotypes of autosomal recessive ataxia with isolated vitamin E deficiency (AVED) (Ouahchi K., et al., Nat. Genet. 1995 9:141-145). The disease is characterized by undetectable or markedly reduced plasma levels of vitamin E, spinocerebellar degeneration, ataxia, areflexia and proprioception loss. Another form of ataxia with related neurological phenotypes is caused by mutations in the SEC14-like Caytaxin gene product of ATCAY (Bomar J. M., et al., Nat. Genet. 2003 35:264-269). Defects in the CRALBP gene product of the RLBP1 gene lead to severe retinal pathologies (Maw M. A., et al., 1997 Nat. Genet. 17:198-200).

SUMMARY OF THE INVENTION

The present invention relates to the surprising finding of previously unknown nanospherical aggregates of SEC14- like family of proteins with their cognate ligands, the methods of production the same and the uses thereof.

Thus, in a first aspect the present invention provides for a nanosphere comprising, preferably consisting of, an equal number of (i) a human SEC14-like protein, and (ii) a cognate ligand of said SEC14-like protein. Preferably, said equal number is of 3 to 60, further preferably, said equal number is of 9 to 60. In a very preferred embodiment of the present invention, said human SEC14-like protein is selected from (a) α-tocopherol transfer protein (α-TTP); (b) Cellular retinaldehyde binding protein (CRALBP); (c) Clavesin1 (CLVS1); (d) Clavesin2 (CLVS2); and (e) alpha-tocopherol transfer protein like (TTPAL).

In further aspects, the present invention provides for methods of producing the inventive nanospheres and uses of the inventive nanospheres.

Thus, in a further aspect, the present invention provides for a method of producing a nanosphere comprising, preferably consisting of, an equal number of (i) a human SEC14-like protein, and (ii) a cognate ligand of said SEC14-like protein, wherein said method comprises the steps of (a) providing said SEC14-like protein in an aqueous solution I, wherein the concentration of said SEC14-like protein in said solution I is 1 µM to 5 mM, and wherein the pH of said solution I is 6 to 9, and wherein preferably said solution I comprises a salt, wherein the concentration of said salt is 10 mM to 500 mM; (b) providing said cognate ligand of SEC14-like protein in a solution II, wherein the concentration of said cognate ligand of SEC14-like protein in said solution I is 5 µM to 500 mM, and wherein the solvent of said solution II is a water soluble solvent; (c) generating a solution III by combining said solution I and said solution II, wherein the ratio of the concentration of said SEC14-like protein and the concentration of said cognate ligand of said SEC14-like protein in said solution III is of between 4:1 to 1:4 (molar/molar), and wherein the volume of said water soluble solvent in said solution III is of between 0.5-8% (vol/vol); (d) allowing said SEC14-like protein and said cognate ligand of said SEC14-like protein to assemble into a nanosphere; (e) separating said nanosphere from said solution III; (f) optionally purifying said nanosphere.

In again a further aspect, the present invention provides for a method of producing a nanosphere comprising, preferably consisting of, an equal number of: (i) a human SEC14-like protein, and (ii) a cognate ligand of said SEC14-like protein; wherein said method comprises the steps of (a) providing said SEC14-like protein in an aqueous solution I, wherein the concentration of said SEC14-like protein in said solution I is 1 µM to 5 mM, and wherein the pH of said solution I is 6 to 9; (b) providing said cognate ligand of SEC14-like protein in an aqueous solution II, wherein the concentration of said cognate ligand of SEC14-like protein in said solution I is 5 µM to 500 mM; and wherein said solution II comprises a detergent; (c) generating a solution III by combining said solution I and said solution II, wherein the ratio of the concentration of said SEC14-like protein and the concentration of said cognate ligand of said SEC14-like protein in said solution III is of between 4:1 to 1:4 (molar/molar); (d) removing said detergent from said solution III, wherein removing said detergent from said solution III allows said SEC14-like protein and said cognate ligand of said SEC14-like protein to assemble into a nanosphere; (e) separating said nanosphere from said solution III; (f) optionally purifying said nanosphere.

In again a further aspect, the present invention provides for a method of producing a nanosphere comprising, preferably consisting of, an equal number of: (i) a human SEC14-like protein, and (ii) a cognate ligand of said SEC14-like protein; wherein said method comprises the steps of (a) providing said SEC14-like protein in an aqueous solution I, wherein the concentration of said SEC14-like protein in said solution I is 1 µM to 5 mM, and wherein the pH of said solution I is 6 to 9, and wherein preferably said solution I comprises a salt, wherein the concentration of said salt is 10 mM to 500 mM; (b) providing said cognate ligand of SEC14-like protein in a solution II, wherein the concentration of said cognate ligand of SEC14-like protein in said solution I is 5 µM to 500 mM, and wherein the solvent of said solution II is a water soluble solvent; (c) generating a solution III by combining said solution I and said solution II, wherein the ratio of the concentration of said SEC14-like protein and the concentration of said cognate ligand of said SEC14-like protein in said solution III is of between 4:1 to 1:4 (molar/molar), and wherein the volume of said water soluble solvent in said solution III is of between 0.5-8% (vol/vol); (d) allowing said SEC14-like protein and said cognate ligand of said SEC14-like protein to form monomeric complexes consisting of one of said SEC14-like protein and one of said cognate ligand of said SEC14-like protein; (e) separating said monomeric complexes from said solution III; (f) optionally purifying said monomeric complexes; (g) generating an aqueous solution IV, wherein said solution IV comprises said monomeric complexes, and wherein the concentration of said monomeric complex in said solution IV is 5 mg/ml to 50 mg/ml; and wherein the pH of said solution IV is 6 to 9, and wherein preferably said solution IV comprises a salt, wherein the concentration of said salt is 10 mM to 500 mM; (h) allowing said monomeric complexes to form crystals of said nanosphere.

In again a further aspect, the present invention provides for a method of producing a nanosphere comprising, preferably consisting of, an equal number of: (i) a human SEC14-like protein, and (ii) a cognate ligand of said SEC14-like protein; wherein said method comprises the steps of (a) providing said SEC14-like protein in an aqueous solution I, wherein the concentration of said SEC14-like protein in said solution I is 1 µM to 5 mM, and wherein the pH of said solution I is 6 to 9; (b) providing said cognate ligand of SEC14-like protein in an aqueous solution II, wherein the concentration of said cognate ligand of SEC14-like protein in said solution I is 5 µM to 500 mM; and wherein said solution II comprises a detergent; (c) generating a solution III by combining said solution I and said solution II, wherein the ratio of the concentration of said SEC14-like protein and the concentration of said cognate ligand of said SEC14-like protein in said solution III is of between 4:1 to 1:4 (molar/molar); (d) removing said detergent from said solution III, wherein removing said detergent from said solution III allows said SEC14-like protein and said cognate ligand of said SEC14-like protein to form monomeric complexes consisting of one of said SEC14-like protein and one of said cognate ligand of said SEC14-like protein; (e) separating said monomeric complexes from said solution III; (f) optionally purifying said monomeric complexes; (g) generating an aqueous solution IV, wherein said solution IV comprises said monomeric complexes, and wherein the concentration of said monomeric complex in said solution IV is 5 mg/ml to 50 mg/ml, and wherein the pH of said solution IV is 6 to 9, and wherein preferably said solution IV comprises a salt, and wherein the concentration of said salt is 10 mM to 500 mM; (h) allowing said monomeric complexes to form crystals of said nanosphere.

In again a further aspect, the present invention provides for a pharmaceutical composition comprising (a) the nanosphere of the present invention; and (b) a pharmaceutically acceptable carrier.

In again a further aspect, the present invention provides for the nanosphere or the pharmaceutical composition of the present invention for use in a method of the treatment or prevention, preferably of the treatment, of Ataxia with Vitamin E Deficiency (AVED), muscle dystrophy, hypolipidemia, hypolipoproteinemia, dyslipidemia, human infertility, impaired wound healing or an inflammatory disease, wherein preferably said inflammatory disease is arthritis.

Further aspects and preferred embodiments of the present invention will become apparent as this description proceeds.

DESCRIPTION OF FIGURES

FIG. 8: A) Mostly hydrophobic residues are clustered in a characteristic sequence pattern leading to the trimeric forms in α-TTP-α-Tol nanospheres. A highly similar pattern of hydrophobic residues is present in the primary sequence of CRALBP (SEQ ID NO:8 and SEQ ID NO:9). B) Primary sequence alignment of the N-terminal segment of α-TTP (aa's 47-90) and related segments in other SEC14-like proteins using the MULTALIN webservice (Corpet, F.; Nucleic Acids Res. 1988 16:10881-10890). Conserved or semi-conserved residues are depicted in light gray. The mostly hydrophobic residues of the characteristic sequence pattern are marked by filled triangles (SEQ ID NO:10, SEQ ID NO:11, SEQ ID NO:12 SEQ ID NO:13 and SEQ ID NO:14). C) PSIPRED based comparison of the secondary helix-loop-helix structures of α-TTP (aa's 47-90) and of CRALBP (aa's 91-123) reveal high structural similarity (SEQ ID NO: 15 and SEQ ID NO: 16).

FIG. 9: Depicted are the primary sequences of preferred SEC14-like proteins with the residues of the characteristic sequence patterns being highlighted in light gray.

DETAILED DESCRIPTION OF THE INVENTION

Figure 1A:
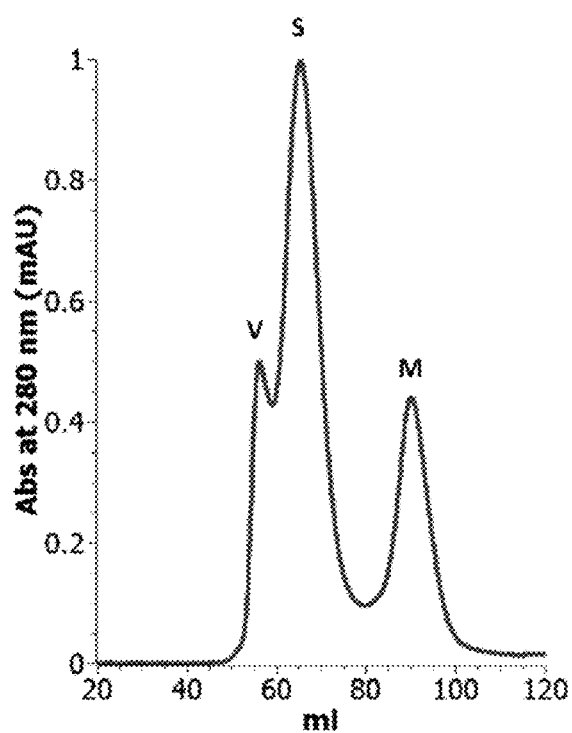
FIG. 1: A) Preparative SEC trace of a mixture of cognate ligand-complexes composed of monomeric α-TTP-α-Tol and of α-TTP-α-Tol nanospheres comprising α-TTP trimers. Peak S represents α-TTP-α-Tol nanospheres centering at a retention volume that correlates to a mass of 0.76 Mda and peak M represents monomeric α-TTP-α-Tol that correlates to a mass of 32 kDa. Peak V contains highly aggregated protein that centers at the column's void volume. B) Analytial SEC traces of apo-α-TTP (black trace) and of holo-α-TTP representing a mixture of cognate ligand-complexes composed of monomeric α-TTP-α-Tol and of α-TTP-α-Tol nanospheres comprising α-TTP trimers (grey trace). The black trace of apo-α-TTP indicates the presence of dimeric apo-α-TTP centering at a retention volume that correlates to a mass of 64 kDa and of monomeric apo-α-TTP centering at a retention volume that correlates to a mass of 32 kDa. The grey holo-α-TTP trace indicates the presence of α-TTP-α-Tol nanospheres centering at a retention volume that correlates to a mass of 0.76 Mda and of monomeric α-TTP-α-Tol that correlates to a mass of 32 kDa. A minor peak D is visible most probably consisting of cognate ligand free dimeric apo-α-TTP that centers at a retention volume that correlates to a mass of 64 kDa.

Unless defined otherwise, all technical and scientific terms used herein have the same meanings as commonly understood by one of ordinary skill in the art to which this invention belongs.

Nanosphere: The term "nanosphere", as used herein, refers to a composition, typically and preferably a polyhedral structure, formed by a number of a SEC14-like protein and an equally number of the cognate ligand of said SEC14-like protein. Typically and preferably, said number is at least 3 and at most 60. Further preferably, said number is at least 9 and at most 60. Again further preferably, said equal number of said SEC14-like protein and the cognate ligand of said SEC14-like protein is a multiple of 3, and wherein further preferably said equal number is 3, 9, 12, 24, 36, 48 and 60, again further preferably 9, 12, 24, 36, 48 and 60. Again further preferably, said equal number of said SEC14-like protein and the cognate ligand of said SEC14-like protein is a multiple of 3, and said number is at least 3 and at most 60, wherein further preferably said equal number is 3, 9, 12, 24, 36, 48 and 60, again further preferably 9, 12, 24, 36, 48 and 60. Typically and preferably, said polyhedral structure is of a size of between 5 nm and 60 nm, preferably of a size of between 7 nm and 55 nm, and further preferably of a size of between 9 nm and 48 nm as determined, preferably by dynamic light scattering in a manner as described in present Example 3E. Thus, typically and preferably the term "nanosphere", as used herein, refers to a polyhedral structure of a size of between 5 nm and 60 nm, preferably of a size of between 7 nm and 55 nm, and further preferably of a size of between 9 nm and 48 nm, as preferably determined by dynamic light scattering, and further preferably as described in present Example 3E, and wherein said polyhedral structure is formed by at least three, further preferably said polyhedral structure is formed by at least nine, further preferably by at least twelve or again further preferably by at least 24, 36, 48 or 60 copies of a SEC14-like protein and an equal number of the cognate ligand of said SEC14-like protein. Typically and preferably, said regular number of equal SEC14-like proteins form a hollow protein coat with said polyhedral structure of a size of between 5 nm and 60 nm, preferably of a size of between 7 nm and 55 nm, and further preferably of a size of between 9 nm and 48 nm, as preferably determined by dynamic light scattering, and further preferably as described in present Example 3E, and in which polyhedral structure the equal number of the cognate ligand of said SEC14-like protein is aggregated. Thus, the stoichiometry in said nanosphere of said SEC14-like protein and the cognate ligand of said SEC14-like protein is 1:1. Typically and preferably, said nanospheres are composed of one type of SEC14-like protein and an equal number of the cognate ligand of said SEC14-like protein. Typically and preferably, the equal SEC14-like protein building blocks forming said hollow coat with said polyhedral structure are also termed herein "protomers".

SEC14-like protein: The term "SEC14-like protein" or "SEC14-like family of protein", as interchangeably as used herein, refers to a protein structural domain (Sha Bi, et al., Nature. 1998 391:506-10) designated CRAL-TRIO that binds, typically and preferably small lipophilic, molecules (Panagabko C, et al., Biochemistry 2003 42:6467-6474). The CRAL-TRIO lipid-binding domain is a $\alpha/\beta$ domain, which forms a large hydrophobic pocket. Its pocket floor is constituted by six $\beta$-strands with strands 2, 3, 4 and 5 constituting a parallel beta sheet and with strands 1 and 6 being anti-parallel. The sides of the cavity are formed by $\alpha$-helices. The CRAL-TRIO domain may either constitute all of the protein or only part of it (Sha B1, et al., Nature. 1998 391:506-10; Panagabko C, et al., Biochemistry 2003 42:6467-6474). Typically and preferably, the cognate ligand free form of the SEC14-like protein is also termed herein as the "apo" form of said SEC14-like protein.

A cognate ligand of a SEC14-like protein: The term "a cognate ligand of a SEC14-like protein", as used herein, refers to a molecule, typically and preferably to a lipid, that binds to a CRAL-TRIO lipid binding pocket with at least nanomolar affinity of typically and preferably 1-100 nM, further typically and preferably with an affinity of 6-60 nM, and which molecule is typically and preferably functionally associated with the SEC14-like protein. Functionally associated: The term "functionally associated", as used herein, refers to the physiological function of the SEC14-like protein that critically depends on the binding of the physiological cognate ligand, termed herein cognate ligand, with at least nanomolar affinity of typically and preferably 1-100 nM, further typically and preferably with an affinity of 6-60 nM. By way of example, R,R,R-$\alpha$-tocopherol represents a cognate ligand of $\alpha$-tocopherol transfer protein ($\alpha$-TTP) and R,R,R-$\alpha$-tocopherol represents one of the most powerful fat-soluble antioxidants.

Bound: The term "bound", as used herein, refers to all possible ways, preferably chemical interactions, by which two molecules are joined together. Chemical interactions include covalent and non-covalent interactions. Typical examples for non-covalent interactions are ionic interactions, hydrophobic interactions or hydrogen bonds, whereas covalent interactions are based on covalent bonds. In preferred embodiments, each of said SEC14-like protein is bound to one of said at least one cognate ligand of said SEC14-like protein by way of at least one covalent or at least one non-covalent interaction. Further preferably, each of said SEC14-like protein is bound to one of said at least one cognate ligand of said SEC14-like protein by way of at least one non-covalent interaction.

Sequence identity: The sequence identity of two given amino acid sequences is determined based on an alignment of both sequences. Algorithms for the determination of sequence identity are available to the artisan. Preferably, the sequence identity of two amino acid sequences is determined using publicly available computer homology programs such as the "BLAST" program (http://blast.ncbi.nlm.nih.gov/Blast.cgi) or the "CLUSTALW" (http://www.genome.jp/tools/clustalw/), and hereby preferably by the "BLAST" program provided on the NCBI homepage at http://blast.ncbi.nlm.nih.gov/Blast.cgi, using the default settings provided therein. Typical and preferred standard settings are: expect threshold: 10; word size: 3; max matches in a query range: 0; matrix: BLOSUM62; gap costs: existence 11, extension 1; compositional adjustments: conditional compositional score matrix adjustment.

Position corresponding to residues . . . . The position on an amino acid sequence, which is corresponding to given residues of another amino acid sequence can be identified by sequence alignment, typically and preferably by using the BLASTP algorithm, most preferably using the standard settings. Typical and preferred standard settings are: expect threshold: 10; word size: 3; max matches in a query range: 0; matrix: BLOSUM62; gap costs: existence 11, extension 1; compositional adjustments: conditional compositional score matrix adjustment. A very preferred determination of the "position corresponding to residues . . . " is outlined in FIG. 8A and FIG. 8B by way of the SEC14-like proteins $\alpha$-TTP and CRALBP which corresponds a preferred embodiment of the present invention.

Effective amount: The term "effective amount", as used herein, refers to an amount necessary or sufficient to realize a desired biologic effect. Preferably, the term "effective amount" refers to an amount of a nanosphere of the present invention that (i) treats or prevents the particular disease, medical condition, or disorder, (ii) attenuates, ameliorates, or eliminates one or more symptoms of the particular disease, medical condition, or disorder, or (iii) prevents or delays the onset of one or more symptoms of the particular disease, medical condition, or disorder described herein. An effective amount of the inventive nanosphere or said pharmaceutical composition, would be the amount that achieves this selected result, and such an amount could be determined as a matter of routine by a person skilled in the art. The effective amount can vary depending on the particular composition being administered and the size of the subject. One of ordinary skill in the art can empirically determine the effective amount of a particular composition of the present invention without necessitating undue experimentation.

The present invention relates to the surprising finding of previously unknown nanospherical aggregates of SEC14-like family of proteins with their cognate ligands, the methods of production the same and the uses thereof.

Thus, in a first aspect the present invention provides for a nanosphere comprising, preferably consisting of, an equal number of (i) a human SEC14-like protein, and (ii) a cognate ligand of said SEC14-like protein. Preferably, said equal number is of 3 to 60. Further preferably, said equal number is of 9 to 60.

In a very preferred embodiment of the present invention, said equal number is a multiple of 3. In a further very preferred embodiment of the present invention, said equal number is a multiple of 3, and said equal number is of 3 to 60. Thus, in a further very preferred embodiment of the present invention, said equal number is a multiple of 3, and said equal number is of 3, 6, 9, 12, 15, 18, 21, 24, 27, 30, 33, 36, 39, 42, 45, 48, 51, 54, 57 or 60.

In a very preferred embodiment of the present invention, said equal number is 3, 9, 12, 24, 36, 48 or 60. In a further very preferred embodiment of the present invention, said equal number is 9, 12, 24, 36, 48 or 60. In a further very preferred embodiment of the present invention, said equal number is 24 or 48.

In an again very preferred embodiment of the present invention, said human SEC14-like protein is selected from (a) α-tocopherol transfer protein (α-TTP); (b) Cellular retinaldehyde binding protein (CRALBP); (c) Clavesin1 (CLVS1); (d) Clavesin2 (CLVS2); and (e) alpha-tocopherol transfer protein like (TTPAL).

In an again very preferred embodiment of the present invention, said SEC14-like protein is α-tocopherol transfer protein (α-TTP), wherein preferably said equal number is 24. Preferably said cognate ligand of said α-tocopherol transfer protein (α-TTP) is a tocopherol, wherein preferably said tocopherol is α-tocopherol and wherein further preferably said α-tocopherol is R,R,R-α-tocopherol.

In an again very preferred embodiment of the present invention, said SEC14-like protein is α-tocopherol transfer protein (α-TTP) and said cognate ligand of said α-tocopherol transfer protein (α-TTP) is α-tocopherol, and wherein said equal number is of 3 to 60, and wherein preferably said α-tocopherol is R,R,R-α-tocopherol.

In an again very preferred embodiment of the present invention, said SEC14-like protein is α-tocopherol transfer protein (α-TTP) and said cognate ligand of said α-tocopherol transfer protein (α-TTP) is α-tocopherol, and wherein said equal number is of 9 to 60, and wherein preferably said α-tocopherol is R,R,R-α-tocopherol.

In an again very preferred embodiment of the present invention, said SEC14-like protein is α-tocopherol transfer protein (α-TTP) and said cognate ligand of said α-tocopherol transfer protein (α-TTP) is R,R,R-α-tocopherol, and said equal number is of 3 to 60, wherein preferably said equal number is 3, 9, 12, 24, 36, 48 or 60. In a further very preferred embodiment of the present invention, said equal number is 24 or 48.

In an again very preferred embodiment of the present invention, said SEC14-like protein is α-tocopherol transfer protein (α-TTP) and said cognate ligand of said α-tocopherol transfer protein (α-TTP) is R,R,R-α-tocopherol, and said equal number is of 9 to 60, wherein preferably said equal number is 9, 12, 24, 36, 48 or 60. In a further very preferred embodiment of the present invention, said equal number is 24 or 48.

In an again very preferred embodiment, the present invention provides for a nanosphere comprising, preferably consisting of, an equal number of (i) a human SEC14-like protein, and (ii) a cognate ligand of said SEC14-like protein, wherein said equal number is a multiple of 3, and wherein preferably said number is of 3 to 60, and wherein said human SEC14-like protein is selected from (a) α-tocopherol transfer protein (α-TTP); (b) Cellular retinaldehyde binding protein (CRALBP); (c) Clavesin1 (CLVS1); (d) Clavesin2 (CLVS2); and (e) alpha-tocopherol transfer protein like (TTPAL).

In an again very preferred embodiment of the present invention, said SEC14-like protein is Cellular retinaldehyde binding protein (CRALBP). Preferably said cognate ligand of said CRALBP is a cis-retinol or a cis retinal, wherein further preferably said cis-retinol or said cis retinal is selected from 9-cis-retinal, 11-cis-retinal, 9,13-dicis-retinal, 9-cis-retinol, 11-cis-retinol and 9,13-dicis-retinol. In a very preferred embodiment of the present invention, said cognate ligand of said CRALBP is 9-cis-retinal. In a further very preferred embodiment of the present invention, said cognate ligand of said CRALBP is 11-cis-retinal. In another preferred embodiment of the present invention, said cognate ligand of said CRALBP is 9-cis-retinol. In again another preferred embodiment of the present invention, said cognate ligand of said CRALBP is 11-cis-retinol. In again another embodiment of the present invention, said cognate ligand of said CRALBP is 9,13-dicis-retinal. In again another embodiment of the present invention, said cognate ligand of said CRALBP is 9,13-dicis-retinol.

In a preferred embodiment of the present invention, said SEC14-like protein is a protein comprising an amino acid sequence selected from (a) SEQ ID NO:3 (α-TTP HUMAN); (b) SEQ ID NO:4 (CRALBP HUMAN); (c) SEQ ID NO:5 (CLVS1 HUMAN); (d) SEQ ID NO:6 (CLVS2 HUMAN); and (e) SEQ ID NO:7 (TTPAL HUMAN).

In another preferred embodiment of the present invention, said SEC14-like protein comprises an amino acid sequence stretch, wherein said amino acid sequence stretch has the amino acid sequence selected from (a) amino acids 56 to 74 of SEQ ID NO:3; (b) amino acids 100 to 118 of SEQ ID NO:4; (c) amino acids 80 to 98 SEQ ID NO:5; (d) amino acids 58 to 76 SEQ ID NO:6; and (e) amino acids 85 to 103 SEQ ID NO:7.

In a further preferred embodiment of the present invention, the amino acid sequence of said SEC14-like protein comprises (a) an amino acid residue selected from L and I on the position of said amino acid sequence of said SEC14-like protein which corresponds to the position 56 of SEQ ID NO:3; (b) the amino acid residue F on the position of said amino acid sequence of said SEC14-like protein which corresponds to the position 61 of SEQ ID NO:3; (c) an amino acid residue selected from L, V, Q, H and Y on the position of said amino acid sequence of said SEC14-like protein which corresponds to the position 63 of SEQ ID NO:3; (d) an amino acid residue selected from W, Y, F and L on the position of said amino acid sequence of said SEC14-like protein which corresponds to the position 67 of SEQ ID NO:3; (e) the amino acid residue L on the position of said amino acid sequence of said SEC14-like protein which corresponds to the position 70 of SEQ ID NO:3; or (f) an amino acid residue selected from Y, V, F and H on the position of said amino acid sequence of said SEC14-like protein which corresponds to the position 74 of SEQ ID NO:3; wherein said amino acid sequence of said SEC14-like protein comprises at least two, preferably at least three, further preferably at least four, again further preferably at least five of any one of said amino acid residues of (a)-(f); and wherein preferably at least four amino acid residues of any one of (a)-(f) of said amino acid sequence of a first of said number of SEC14-like protein comprised by said nanosphere is bound to at least four amino acid residues of any one of (a)-(f) of said amino acid sequence of a second and of a third of said number of SEC14-like protein comprised by said nanosphere.

In a further preferred embodiment of the present invention, said SEC14-like protein comprises an amino acid sequence, wherein said amino acid sequence of said SEC14-like protein comprises (a) an amino acid residue selected from L and I on the position which corresponds to the position 56 of SEQ ID NO:3; (b) the amino acid residue F on the position which corresponds to the position 61 of SEQ ID NO:3; (c) an amino acid residue selected from L, V, Q, H and Y on the position which corresponds to the position 63 of SEQ ID NO:3; (d) an amino acid residue selected from W, Y, F and L on the position which corresponds to the position 67 of SEQ ID NO:3; (e) the amino acid residue L on the position which corresponds to the position 70 of SEQ ID NO:3; or (f) an amino acid residue selected from Y, V, F and H on the position which corresponds to the position 74 of SEQ ID NO:3; wherein said amino acid sequence of said SEC14-like protein comprises at least two, preferably at least three, further preferably at least four, again further preferably at least five of any one of said amino acid residues of (a)-(f); and wherein preferably at least four amino acid residues of any one of (a)-(f) of said amino acid sequence of a first of said number of SEC14-like protein comprised by said nanosphere is bound to at least four amino acid residues of any one of (a)-(f) of said amino acid sequence of a second and of a third of said number of SEC14-like protein comprised by said nanosphere.

Without being bound by this theory, it is believed that the aforementioned amino sequence residues and patterns favor the formation of trimeric aggregates of said SEC14-like protein, which in turn favor the formation of the inventive nanospheres. Moreover, and again without being bound by this theory, it is believed that the process of sequestration of the cognate ligand of said SEC14-like protein is accompanied by conformational rearrangements in the SEC14-like protein including a closing movement of a helical element of its C-terminal region designated mobile gate. Thus, it is believed, without being bound by this theory, that the formation of trimeric aggregates and in particular the inventive nanospheres depend on conformational rearrangements within the N-terminal region of the SEC14-like protein that effect the unmasking of the helix-turn-helix segment that carries the aforementioned amino sequence residues and patterns otherwise inaccessible to solvent. Typically, the loading procedure of said cognate ligand of said SEC14-like protein yields mixtures of monomeric and nanospheric protein-ligand complexes that can be both purified by suitable chromatrographic methods such as size exclusion chromatography and/or anionic exchange chromatography.

Furthermore, we have shown that the inventive nanospheres, in particular the inventive nanospheres of the SEC14-like protein alpha-TTP do efficiently transcytose through primary human umbilical vein endothelial cells. This process was shown to be highly specific by demonstrating the absence of transcytosis of the same nanospheres through a standard epithelial cell line. As a consequence, the inventive nanospheres are expected to be highly suitable to overcome the blood brain barrier when injected into the blood stream.

In a preferred embodiment of the present invention, each of said cognate ligand of said SEC14-like protein is bound to one of said SEC14-like protein by way of at least one non-covalent interaction, wherein preferably each of said cognate ligand of said SEC14-like protein is bound to only one of said SEC14-like protein by way of at least one non-covalent interaction.

In a further aspect, the present invention provides for a method of producing a nanosphere comprising, preferably consisting of, an equal number of (i) a human SEC14-like protein, and (ii) a cognate ligand of said SEC14-like protein, wherein preferably said equal number is 3 to 60, wherein said method comprises the steps of (a) providing said SEC14-like protein in an aqueous solution I, wherein the concentration of said SEC14-like protein in said solution I is 1 µM to 5 mM, and wherein the pH of said solution I is 6 to 9, and wherein preferably said solution I comprises a salt, wherein the concentration of said salt is 10 mM to 500 mM; (b) providing said cognate ligand of SEC14-like protein in a solution II, wherein the concentration of said cognate ligand of SEC14-like protein in said solution I is 5 µM to 500 mM, and wherein the solvent of said solution II is a water soluble solvent; (c) generating a solution III by combining said solution I and said solution II, wherein the ratio of the concentration of said SEC14-like protein and the concentration of said cognate ligand of said SEC14-like protein in said solution III is of between 4:1 to 1:4 (molar/molar), and wherein the volume of said water soluble solvent in said solution III is of between 0.5-8% (vol/vol); (d) allowing said SEC14-like protein and said cognate ligand of said SEC14-like protein to assemble into a nanosphere; (e) separating said nanosphere from solution III; (f) optionally purifying said nanosphere.

Further preferred embodiment of the inventive methods include the preferred and very preferred embodiments of the inventive nanosphere. In particular, in a very preferred embodiment, said equal number is a multiple of 3, and wherein preferably said number is of 3 to 60, and wherein said human SEC14-like protein is selected from (a) α-tocopherol transfer protein (α-TTP); (b) Cellular retinaldehyde binding protein (CRALBP); (c) Clavesin1 (CLVS1); (d) Clavesin2 (CLVS2); and (e) alpha-tocopherol transfer protein like (TTPAL).

In a further aspect, the present invention provides for a method of producing a nanosphere comprising, preferably consisting of, an equal number of (i) a human SEC14-like protein, and (ii) a cognate ligand of said SEC14-like protein, wherein preferably said equal number is 9 to 60, wherein said method comprises the steps of (a) providing said SEC14-like protein in an aqueous solution I, wherein the concentration of said SEC14-like protein in said solution I is 1 µM to 5 mM, and wherein the pH of said solution I is 6 to 9, and wherein preferably said solution I comprises a salt, wherein the concentration of said salt is 10 mM to 500 mM;

(b) providing said cognate ligand of SEC14-like protein in a solution II, wherein the concentration of said cognate ligand of SEC14-like protein in said solution I is 5 µM to 500 mM, and wherein the solvent of said solution II is a water soluble solvent; (c) generating a solution III by combining said solution I and said solution II, wherein the ratio of the concentration of said SEC14-like protein and the concentration of said cognate ligand of said SEC14-like protein in said solution III is of between 4:1 to 1:4 (molar/molar), and wherein the volume of said water soluble solvent in said solution III is of between 0.5-8% (vol/vol); (d) allowing said SEC14-like protein and said cognate ligand of said SEC14-like protein to assemble into a nanosphere; (e) separating said nanosphere from said solution III; (f) optionally purifying said nanosphere.

Further preferred embodiment of the inventive methods include the preferred and very preferred embodiments of the inventive nanosphere. In particular, in a very preferred embodiment, said equal number is a multiple of 3, and wherein preferably said number is of 3 to 60, and wherein said human SEC14-like protein is selected from (a) α-tocopherol transfer protein (α-TTP); (b) Cellular retinaldehyde binding protein (CRALBP); (c) Clavesin1 (CLVS1); (d) Clavesin2 (CLVS2); and (e) alpha-tocopherol transfer protein like (TTPAL).

In a further preferred embodiment, the concentration of said SEC14-like protein in said solution I is 0.1 mM to 1 mM, and further preferably the concentration of said SEC14-like protein in said solution I is 0.25 mM to 0.75 mM.

In a further preferred embodiment, the pH of said solution I is 7 to 8. Preferably said solution I comprises a salt, wherein the concentration of said salt is 10 mM to 500 mM. Further preferred, the concentration of said salt is 30 mM to 350 mM, and further preferably the concentration of said salt is 100 mM to 250 mM.

In a further preferred embodiment, said salt is selected from a mono-, di-, tri- or tetravalent inorganic or organic salt, and wherein further preferably said salt is selected from a di-, tri- or tetravalent inorganic or organic salt, and wherein again further preferably said salt comprises a divalent, tri, or tetravalent anion selected from $HPO_4^{2-}$, $SO_4^{2-}$, tartrate, malonate, D-myo-inositol 1,4,5-triphosphate and D-myo-inositol 1,3,4,5-tetrakis(phosphate) potassium salt.

In a further preferred embodiment, said concentration of said cognate ligand of SEC14-like protein in said solution I is 30 µM to 300 mM, further preferably the concentration of said cognate ligand of SEC14-like protein in said solution I is 20 µM to 200 mM.

The solvent of said solution II is a water soluble solvent. It is within the scope of the present invention that the water soluble solvent used for solution II may comprise minor amounts, i.e. up to 10% (v/v) of water even though typically and preferably said water soluble solvent does not comprise any additional amounts of water other than the minor amount of water typically comprised in said water soluble solvent when supplied by the manufacturer. Further preferably, said water soluble solvent dose not comprise more than 8% (v/v), preferably more than 7% (v/v), further preferably more than 5% (v/v) of water.

In a preferred embodiment of the present invention, said water soluble solvent is selected from methanol, ethanol, isopropanol, propanol, butanol, dimethyl sulfoxide (DMSO), tetrahydrofuran (THF), dioxan, methylpentane diol and glycerol; further preferably said water soluble solvent is selected from ethanol, isopropanol and dimethyl sulfoxide (DMSO).

In a preferred embodiment of the present invention, said ratio of the concentration of said SEC14-like protein and the concentration of said cognate ligand of said SEC14-like protein in said solution III is of between 3:1 to 1:3 (molar/molar), and preferably the ratio of the concentration of said SEC14-like protein and the concentration of said cognate ligand of said SEC14-like protein in said solution III is of between 2:1 to 1:2 (molar/molar).

In another preferred embodiment of the present invention, said volume of said water soluble solvent in said solution III is of between 1-5% (vol/vol), and preferably the volume of said water soluble solvent in said solution III is of between 2-4% (vol/vol).

In a preferred embodiment of the present invention, said allowing said SEC14-like protein and said cognate ligand of said SEC14-like protein to assemble into a nanosphere is effected by keeping said solution III at a temperature of 4-37° C., preferably at room temperature, for a period of 1 h to 24 h, preferably for a period of 12 to 24 h.

In a further preferred embodiment of the present invention, said separating said nanosphere from said solution III is effected by size exclusion chromatography or anionic exchange chromatography, preferably by size exclusion chromatography.

In another preferred embodiment of the present invention, said purifying said nanosphere is effected by size exclusion chromatography or anionic exchange chromatography, preferably by size exclusion chromatography.

In a further aspect, the present invention provides for a method of producing the inventive nanosphere as described herein, wherein said nanosphere comprises, preferably consists of, an equal number of (i) a human SEC14-like protein, and (ii) a cognate ligand of said SEC14-like protein, wherein preferably said equal number is 3 to 60, wherein said method comprises the steps of (a) providing said SEC14-like protein in an aqueous solution I, wherein the concentration of said SEC14-like protein in said solution I is 1 µM to 5 mM, and wherein the pH of said solution I is 6 to 9; (b) providing said cognate ligand of SEC14-like protein in an aqueous solution II, wherein the concentration of said cognate ligand of SEC14-like protein in said solution I is 5 µM to 500 mM; and wherein said solution II comprises a detergent; (c) generating a solution III by combining said solution I and said solution II, wherein the ratio of the concentration of said SEC14-like protein and the concentration of said cognate ligand of said SEC14-like protein in said solution III is of between 4:1 to 1:4 (molar/molar); (d) removing said detergent from said solution III, wherein removing said detergent from said solution III allows said SEC14-like protein and said cognate ligand of said SEC14-like protein to assemble into a nanosphere; (e) separating said nanosphere from said solution III; (f) optionally purifying said nanosphere. Further preferred embodiment of the inventive methods include the preferred and very preferred embodiments of the inventive nanosphere. In particular, in a very preferred embodiment, said equal number is a multiple of 3, and wherein preferably said number is of 3 to 60, and wherein said human SEC14-like protein is selected from (a) α-tocopherol transfer protein (α-TTP); (b) Cellular retinaldehyde binding protein (CRALBP); (c) Clavesin1 (CLVS1); (d) Clavesin2 (CLVS2); and (e) alpha-tocopherol transfer protein like (TTPAL).

In a further aspect, the present invention provides for a method of producing the inventive nanosphere as described herein, wherein said nanosphere comprises, preferably consists of, an equal number of (i) a human SEC14-like protein, and (ii) a cognate ligand of said SEC14-like protein, wherein preferably said equal number is 9 to 60, wherein said method comprises the steps of (a) providing said SEC14-like protein in an aqueous solution I, wherein the concentration of said SEC14-like protein in said solution I is 1 µM to 5 mM, and wherein the pH of said solution I is 6 to 9; (b) providing said cognate ligand of SEC14-like protein in an aqueous solution II, wherein the concentration of said cognate ligand of SEC14-like protein in said solution I is 5 µM to 500 mM; and wherein said solution II comprises a detergent; (c) generating a solution III by combining said solution I and said solution II, wherein the ratio of the concentration of said SEC14-like protein and the concentration of said cognate ligand of said SEC14-like protein in said solution III is of between 4:1 to 1:4 (molar/molar); (d) removing said detergent from said solution III, wherein removing said detergent from said solution III allows said SEC14-like protein and said cognate ligand of said SEC14-like protein to assemble into a nanosphere; (e) separating said nanosphere from said solution III; (f) optionally purifying said nanosphere. Further preferred embodiment of the inventive methods include the preferred and very preferred embodiments of the inventive nanosphere. In particular, in a very preferred embodiment, said equal number is a multiple of 3, and wherein preferably said number is of 3 to 60, and wherein said human SEC14-like protein is selected from (a) α-tocopherol transfer protein (α-TTP); (b) Cellular retinaldehyde binding protein (CRALBP); (c) Clavesin1 (CLVS1); (d) Clavesin2 (CLVS2); and (e) alpha-tocopherol transfer protein like (TTPAL).

Further preferred embodiment of the inventive methods include the preferred and very preferred embodiments of the inventive nanosphere.

In a further preferred embodiment, the concentration of said SEC14-like protein in said solution I is 0.1 mM to 1 mM, and further preferably the concentration of said SEC14-like protein in said solution I is 0.25 mM to 0.75 mM. In a further preferred embodiment, the pH of said solution I is 7 to 8.

In a further preferred embodiment, said concentration of said cognate ligand of SEC14-like protein in said solution I is 30 µM to 300 mM, further preferably the concentration of said cognate ligand of SEC14-like protein in said solution I is 200 µM to 200 mM.

For this inventive method, said solution II comprises a detergent. The detergent serves to solubilize said cognate ligand of SEC14-like protein in said solution II. In a preferred embodiment of the present invention, said detergent is selected from a non-ionic detergent or an anionic detergent. Preferably said non-ionic detergent is selected from octyl beta-D-glucoside, nonyl beta-D-glucoside, decyl beta-D-glucoside, nonyl beta-D-maltoside, decyl beta-D-maltoside, undecyl beta-D-maltoside, dodecyl beta-D-maltoside, Tween 20®, Tween 40®, Tween 80® Triton X100®, Nonidet P40, polyethylenglycol 200. Preferably said anionic detergent is selected from sodium cholate, sodium deoxycholate, sodium glycocholate, sodium deoxyglycocholate and sodium taurocholate.

In a further preferred embodiment, said non-ionic detergent is selected from octyl beta-D-glucoside, nonyl beta-D-glucoside, decyl beta-D-glucoside, nonyl beta-D-maltoside, decyl beta-D-maltoside, undecyl beta-D-maltoside, dodecyl beta-D-maltoside, Tween 20®, Tween 40®, Tween 80® Triton X100, Nonidet P40, polyethylenglycol 200.

In a further very preferred embodiment, said anionic detergent is selected from sodium cholate, sodium deoxycholate, sodium glycocholate, sodium deoxyglycocholate and sodium taurocholate. In a very preferred embodiment, said detergent is an anionic detergent, wherein said anionic detergent is sodium cholate.

The concentration of said detergent used in said solution II can be determined by the skilled person in the art and is based on the knowledge the skilled person in the art since in order to solubilize said cognate ligand of SEC14-like protein in said solution II the concentration is dependent on the nature of the detergent used. Typically and preferably the concentration of said detergent in said solution II is higher the critical micelle concentration (CMC) of said detergent, typically and preferably of said non-ionic detergent or said anionic detergent. Typically and preferably the critical micelle concentration (CMC) of said detergent, typically and preferably of non-ionic detergent or said anionic detergent is equal or higher than 0.5 mM, and wherein further preferably the critical micelle concentration (CMC) of said non-ionic detergent or said anionic detergent is equal or higher than 10 mM.

In a further preferred embodiment, the ratio of the concentration of said SEC14-like protein and the concentration of said cognate ligand of said SEC14-like protein in said solution III is of between 3:1 to 1:3 (molar/molar), and preferably the ratio of the concentration of said SEC14-like protein and the concentration of said cognate ligand of said SEC14-like protein in said solution III is of between 2:1 to 1:2 (molar/molar).

In a further preferred embodiment, said removing of said detergent from said solution III is performed by dialysis; and wherein preferably said removing of said detergent from said solution III by dialysis is performed across a membrane, wherein preferably said membrane comprises a molecular weight cut off of 1 to 25 kD, preferably of 5 to 20 kD, and again further preferably of 10-15 kD. The dialysis is preferably performed with a first buffer, wherein said first buffer comprises a halogenide of an alkaline metal, wherein preferably said halogenide of an alkaline metal is potassium chloride or sodium chloride, and wherein further preferably said halogenide of an alkaline metal is sodium chloride, wherein preferably the concentration of said halogenide of an alkaline metal, preferably said sodium chloride in said first buffer is 1 to 1000 mM, preferably 10 to 500 mM, more preferably 50 to 250 mM, most preferably 100-200 mM.

The dialysis is preferably performed at a temperature of 4° C. to 37° C., and wherein preferably said dialysis is performed over a period of 4 to 24 h.

In a further preferred embodiment, said separating said nanosphere from said solution III is effected by size exclusion chromatography or anionic exchange chromatography, preferably by size exclusion chromatography.

In a further preferred embodiment, said purifying said nanosphere is effected by size exclusion chromatography or anionic exchange chromatography, preferably by size exclusion chromatography.

In again a further aspect, the present invention provides for a method of producing a nanosphere comprising, preferably consisting of, an equal number of: (i) a human SEC14-like protein, and (ii) a cognate ligand of said SEC14-like protein; wherein said method comprises the steps of (a) providing said SEC14-like protein in an aqueous solution I, wherein the concentration of said SEC14-like protein in said solution I is 1 µM to 5 mM, and wherein the pH of said solution I is 6 to 9, and wherein preferably said solution I comprises a salt, wherein the concentration of said salt is 10 mM to 500 mM; (b) providing said cognate ligand of SEC14-like protein in a solution II, wherein the concentration of said cognate ligand of SEC14-like protein in said solution I is 5 µM to 500 mM, and wherein the solvent of said solution II is a water soluble solvent; (c) generating a solution III by combining said solution I and said solution II, wherein the ratio of the concentration of said SEC14-like protein and the concentration of said cognate ligand of said SEC14-like protein in said solution III is of between 4:1 to 1:4 (molar/molar), and wherein the volume of said water soluble solvent in said solution III is of between 0.5-8% (vol/vol); (d) allowing said SEC14-like protein and said cognate ligand of said SEC14-like protein to form monomeric complexes consisting of one of said SEC14-like protein and one of said cognate ligand of said SEC14-like protein; (e) separating said monomeric complexes from solution III; (f) optionally purifying said monomeric complexes; (g) generating an aqueous solution IV, wherein said solution IV comprises said monomeric complexes, and wherein the concentration of said monomeric complex in said solution IV is 5 mg/ml to 50 mg/ml; and wherein the pH of said solution IV is 6 to 9, and wherein preferably said solution IV comprises a salt, wherein the concentration of said salt is 10 mM to 500 mM; (h) allowing said monomeric complexes to form crystals of said nanosphere.

Further preferred embodiment of the inventive methods include the preferred and very preferred embodiments of the inventive nanosphere.

In a further preferred embodiment, the concentration of said SEC14-like protein in said solution I is 0.1 mM to 1 mM, and further preferably the concentration of said SEC14-like protein in said solution I is 0.25 mM to 0.75 mM.

In a further preferred embodiment, the pH of said solution I is 7 to 8. Preferably said solution I comprises a salt, wherein the concentration of said salt is 10 mM to 500 mM. Further preferred, the concentration of said salt is 30 mM to 350 mM, and further preferably the concentration of said salt is 100 mM to 250 mM.

In a further preferred embodiment, said salt is selected from a mono-, di-, tri- or tetravalent inorganic or organic salt, and wherein further preferably said salt is selected from a di-, tri- or tetravalent inorganic or organic salt, and wherein again further preferably said salt comprises a divalent, tri, or tetravalent anion selected from $HPO_4^{2-}$, $SO_4^{2-}$, tartrate, malonate, D-myo-inositol 1,4,5-triphosphate and D-myo-inositol 1,3,4,5-tetrakis(phosphate) potassium salt.

In a further preferred embodiment, said concentration of said cognate ligand of SEC14-like protein in said solution I is 30 µM to 300 mM, further preferably the concentration of said cognate ligand of SEC14-like protein in said solution I is 20 µM to 200 mM.

The solvent of said solution II is a water soluble solvent. It is within the scope of the present invention that the water soluble solvent used for solution II may comprise minor amounts, i.e. up to 10% (v/v) of water even though typically and preferably said water soluble solvent does not comprise any additional amounts of water other than the minor amount of water typically comprised in said water soluble solvent when supplied by the manufacturer. Further preferably, said water soluble solvent dose not comprise more than 8% (v/v), preferably more than 7% (v/v), further preferably more than 5% (v/v) of water.

In a preferred embodiment of the present invention, said water soluble solvent is selected from methanol, ethanol, isopropanol, propanol, butanol, dimethyl sulfoxide (DMSO), tetrahydrofuran (THF), dioxan, methylpentane diol and glycerol; further preferably said water soluble solvent is selected from ethanol, isopropanol and dimethyl sulfoxide (DMSO).

In a preferred embodiment of the present invention, said ratio of the concentration of said SEC14-like protein and the concentration of said cognate ligand of said SEC14-like protein in said solution III is of between 3:1 to 1:3 (molar/molar), and preferably the ratio of the concentration of said SEC14-like protein and the concentration of said cognate ligand of said SEC14-like protein in said solution III is of between 2:1 to 1:2 (molar/molar).

In another preferred embodiment of the present invention, said volume of said water soluble solvent in said solution III is of between 1-5% (vol/vol), and preferably the volume of said water soluble solvent in said solution III is of between 2-4% (vol/vol).

In another preferred embodiment of the present invention, said allowing said SEC14-like protein and said cognate ligand of said SEC14-like protein to form said monomeric complexes is effected by keeping said solution III at a temperature of 4-37° C., preferably at room temperature, for a period of 1 h to 24 h, preferably for a period of 12 to 24 h.

In another preferred embodiment of the present invention, said separating said monomeric complexes from said solution III is effected by size exclusion chromatography or anionic exchange chromatography, preferably by size exclusion chromatography.

In another preferred embodiment of the present invention, said purifying said monomeric complexes is effected by size exclusion chromatography or anionic exchange chromatography, preferably by size exclusion chromatography.

In another preferred embodiment of the present invention, the concentration of said monomeric complex in said solution IV is 10 mg/ml to 40 mg/ml, and preferably the concentration of said monomeric complex in said solution IV is 10 mg/ml to 30 mg/ml, and further preferably the concentration of said monomeric complex in said solution IV is 12 mg/ml to 22 mg/ml. Preferably, the pH of said solution IV is 7 to 8, further preferably the pH of said solution IV is 7.2 to 7.8.

In another preferred embodiment, said solution IV comprises a salt, wherein the concentration of said salt is 10 mM to 500 mM; and preferably said salt is selected from a mono-, di-, tri- or tetravalent inorganic or organic salt. Further preferably said salt is selected from a di-, tri-, or tetravalent inorganic or organic salt, and again further preferably said salt comprises a divalent, tri, or tetravalent anion selected from $HPO_4^{2-}$, $SO_4^{2-}$, tartrate, malonate, D-myo-inositol 1,4,5-triphosphate and D-myo-inositol 1,3,4,5-tetrakis(phosphate) potassium salt.

In another preferred embodiment, said solution IV comprises PEG, wherein the concentration of said PEG is 1% v/v to 30% v/v; and wherein preferably said PEG has a weight average molecular weight of between from 200 to 30'000, further preferably from 200 to 20000 including PEG 200, 400, 800, 2000, 3350 4000, 8000, 12000, 16000.

Said salt and said PEG when comprised in said solution IV represent an amphiphilic precipitant being beneficial and preferred for said solution IV of the present invention. Amphiphilic precipitants and mixtures of amphiphilic precipitants like the preferred one of the present invention are known to the skilled person in the art. Other amphiphilic precipitants and mixtures of amphiphilic precipitants are encompassed within the present invention.

In another preferred embodiment, said allowing said monomeric complexes to form crystals of said nanosphere is effected at constant temperature of 4° C.-37° C., wherein said constant temperature is preferably from 10° C.-20° C. and wherein said temperature is further preferably from 16° C.-19° C.

In a further aspect, the present invention provides for a method of producing the inventive nanosphere as described herein, wherein said nanosphere comprises, preferably consists of, an equal number of (i) a human SEC14-like protein, and (ii) a cognate ligand of said SEC14-like protein, wherein preferably said equal number is 3 to 60, wherein said method comprises the steps of (a) providing said SEC14-like protein in an aqueous solution I, wherein the concentration of said SEC14-like protein in said solution I is 1 µM to 5 mM, and wherein the pH of said solution I is 6 to 9; (b) providing said cognate ligand of SEC14-like protein in an aqueous solution II, wherein the concentration of said cognate ligand of SEC14-like protein in said solution I is 5 µM to 500 mM; and wherein said solution II comprises a detergent; (c) generating a solution III by combining said solution I and said solution II, wherein the ratio of the concentration of said SEC14-like protein and the concentration of said cognate ligand of said SEC14-like protein in said solution III is of between 4:1 to 1:4 (molar/molar); (d) removing said detergent from said solution III, wherein removing said detergent from said solution III allows said SEC14-like protein and said cognate ligand of said SEC14-like protein to form monomeric complexes consisting of one of said SEC14-like protein and one of said cognate ligand of said SEC14-like protein; (e) separating said monomeric complexes from said solution III; (f) optionally purifying said monomeric complexes; (g) generating an aqueous solution IV, wherein said solution IV comprises said monomeric complexes, and wherein the concentration of said monomeric complex in said solution IV is 5 mg/ml to 50 mg/ml, and wherein the pH of said solution IV is 6 to 9, and wherein preferably said solution IV comprises a salt, and wherein the concentration of said salt is 10 mM to 500 mM; (h) allowing said monomeric complexes to form crystals of said nanosphere. Further preferred embodiment of the inventive methods include the preferred and very preferred embodiments of the inventive nanosphere. In particular, in a very preferred embodiment, said equal number is a multiple of 3, and wherein preferably said number is of 3 to 60, and wherein said human SEC14-like protein is selected from (a) α-tocopherol transfer protein (α-TTP); (b) Cellular retinaldehyde binding protein (CRALBP); (c) Clavesin1 (CLVS1); (d) Clavesin2 (CLVS2); and (e) alpha-tocopherol transfer protein like (TTPAL).

In a further aspect, the present invention provides for a method of producing the inventive nanosphere as described herein, wherein said nanosphere comprises, preferably consists of, an equal number of (i) a human SEC14-like protein, and (ii) a cognate ligand of said SEC14-like protein, wherein preferably said equal number is 9 to 60, wherein said method comprises the steps of (a) providing said SEC14-like protein in an aqueous solution I, wherein the concentration of said SEC14-like protein in said solution I is 1 µM to 5 mM, and wherein the pH of said solution I is 6 to 9; (b) providing said cognate ligand of SEC14-like protein in an aqueous solution II, wherein the concentration of said cognate ligand of SEC14-like protein in said solution I is 5 µM to 500 mM; and wherein said solution II comprises a detergent; (c) generating a solution III by combining said solution I and said solution II, wherein the ratio of the concentration of said SEC14-like protein and the concentration of said cognate ligand of said SEC14-like protein in said solution III is of between 4:1 to 1:4 (molar/molar); (d) removing said detergent from said solution III, wherein removing said detergent from said solution III allows said SEC14-like protein and said cognate ligand of said SEC14-like protein to form monomeric complexes consisting of one of said SEC14-like protein and one of said cognate ligand of said SEC14-like protein; (e) separating said monomeric complexes from said solution III; (f) optionally purifying said monomeric complexes; (g) generating an aqueous solution IV, wherein said solution IV comprises said monomeric complexes, and wherein the concentration of said monomeric complex in said solution IV is 5 mg/ml to 50 mg/ml, and wherein the pH of said solution IV is 6 to 9, and wherein preferably said solution IV comprises a salt, and wherein the concentration of said salt is 10 mM to 500 mM; (h) allowing said monomeric complexes to form crystals of said nanosphere. Further preferred embodiment of the inventive methods include the preferred and very preferred embodiments of the inventive nanosphere. In particular, in a very preferred embodiment, said equal number is a multiple of 3, and wherein preferably said number is of 3 to 60, and wherein said human SEC14-like protein is selected from (a) α-tocopherol transfer protein (α-TTP); (b) Cellular retinaldehyde binding protein (CRALBP); (c) Clavesin1 (CLVS1); (d) Clavesin2 (CLVS2); and (e) alpha-tocopherol transfer protein like (TTPAL).

Further preferred embodiment of the inventive methods include the preferred and very preferred embodiments of the inventive nanosphere.

In a further preferred embodiment, the concentration of said SEC14-like protein in said solution I is 0.1 mM to 1 mM, and further preferably the concentration of said SEC14-like protein in said solution I is 0.25 mM to 0.75 mM. In a further preferred embodiment, the pH of said solution I is 7 to 8.

In a further preferred embodiment, said concentration of said cognate ligand of SEC14-like protein in said solution I is 30 µM to 300 mM, further preferably the concentration of said cognate ligand of SEC14-like protein in said solution I is 20 µM to 200 mM.

For this inventive method, said solution II comprises a detergent. The detergent serves to solubilize said cognate ligand of SEC14-like protein in said solution II. In a preferred embodiment of the present invention, said detergent is selected from a non-ionic detergent or an anionic detergent. Preferably said non-ionic detergent is selected from octyl beta-D-glucoside, nonyl beta-D-glucoside, decyl beta-D-glucoside, nonyl beta-D-maltoside, decyl beta-D-maltoside, undecyl beta-D-maltoside, dodecyl beta-D-maltoside, Tween 20®, Tween 40®, Tween 80® Triton X100®, Nonidet P40, polyethylenglycol 200. Preferably said anionic detergent is selected from sodium cholate, sodium deoxycholate, sodium glycocholate, sodium deoxyglycocholate and sodium taurocholate.

In a further preferred embodiment, said non-ionic detergent is selected from octyl beta-D-glucoside, nonyl beta-D-glucoside, decyl beta-D-glucoside, nonyl beta-D-maltoside, decyl beta-D-maltoside, undecyl beta-D-maltoside, dodecyl beta-D-maltoside, Tween 20®, Tween 40®, Tween 80® Triton X100®, Nonidet P40, polyethylenglycol 200.

In a further very preferred embodiment, said anionic detergent is selected from sodium cholate, sodium deoxycholate, sodium glycocholate, sodium deoxyglycocholate and sodium taurocholate. In a very preferred embodiment, said detergent is an anionic detergent, wherein said anionic detergent is sodium cholate.

The concentration of said detergent used in said solution II can be determined by the skilled person in the art and is based on the knowledge the skilled person in the art since in order to solubilize said cognate ligand of SEC14-like protein in said solution II the concentration is dependent on the nature of the detergent used. Typically and preferably the concentration of said detergent in said solution II is higher the critical micelle concentration (CMC) of said detergent, typically and preferably of said non-ionic detergent or said anionic detergent. Typically and preferably the critical micelle concentration (CMC) of said detergent, typically and preferably of non-ionic detergent or said anionic detergent is equal or higher than 0.5 mM, and wherein further preferably the critical micelle concentration (CMC) of said non-ionic detergent or said anionic detergent is equal or higher than 10 mM.

In a further preferred embodiment, the ratio of the concentration of said SEC14-like protein and the concentration of said cognate ligand of said SEC14-like protein in said solution III is of between 3:1 to 1:3 (molar/molar), and preferably the ratio of the concentration of said SEC14-like protein and the concentration of said cognate ligand of said SEC14-like protein in said solution III is of between 2:1 to 1:2 (molar/molar).

In a further preferred embodiment, said removing of said detergent from said solution III is performed by dialysis; and wherein preferably said removing of said detergent from said solution III by dialysis is performed across a membrane, wherein preferably said membrane comprises a molecular weight cut off of 1 to 25 kD, preferably of 5 to 20 kD, and again further preferably of 10-15 kD. The dialysis is preferably performed with a first buffer, wherein said first buffer comprises a halogenide of an alkaline metal, wherein preferably said halogenide of an alkaline metal is potassium chloride or sodium chloride, and wherein further preferably said halogenide of an alkaline metal is sodium chloride, wherein preferably the concentration of said halogenide of an alkaline metal, preferably said sodium chloride in said first buffer is 1 to 1000 mM, preferably 10 to 500 mM, more preferably 50 to 250 mM, most preferably 100-200 mM.

The dialysis is preferably performed at a temperature of 4° C. to 37° C., and wherein preferably said dialysis is performed over a period of 4 to 24 h.

In a further preferred embodiment, said separating said monomeric complexes from said solution III is effected by size exclusion chromatography or anionic exchange chromatography, preferably by size exclusion chromatography.

In a further preferred embodiment, said purifying said monomeric complexes is effected by size exclusion chromatography or anionic exchange chromatography, preferably by size exclusion chromatography.

In another preferred embodiment of the present invention, the concentration of said monomeric complex in said solution IV is 10 mg/ml to 40 mg/ml, and preferably the concentration of said monomeric complex in said solution IV is 10 mg/ml to 30 mg/ml, and further preferably the concentration of said monomeric complex in said solution IV is 12 mg/ml to 22 mg/ml. Preferably, the pH of said solution IV is 7 to 8, further preferably the pH of said solution IV is 7.2 to 7.8.

In another preferred embodiment, said solution IV comprises a salt, wherein the concentration of said salt is 10 mM to 500 mM; and preferably said salt is selected from a mono-, di-, tri- or tetravalent inorganic or organic salt. Further preferably said salt is selected from a di-, tri-, or tetravalent inorganic or organic salt, and again further preferably said salt comprises a divalent, tri, or tetravalent anion selected from $HPO_4^{2-}$, $SO_4^{2-}$, tartrate, malonate, D-myo-inositol 1,4,5-triphosphate and D-myo-inositol 1,3,4,5-tetrakis(phosphate) potassium salt.

In another preferred embodiment, said solution IV comprises PEG, wherein the concentration of said PEG is 1% v/v to 30% v/v; and wherein preferably said PEG has a weight average molecular weight of between from 200 to 30'000, further preferably from 200 to 20000 including PEG 200, 400, 800, 2000, 3350 4000, 8000, 12000, 16000.

Said salt and said PEG when comprised in said solution IV represent an amphiphilic precipitant being beneficial and preferred for said solution IV of the present invention. Amphiphilic precipitants and mixtures of amphiphilic precipitants like the preferred one of the present invention are known to the skilled person in the art. Other amphiphilic precipitants and mixtures of amphiphilic precipitants are encompassed within the present invention.

In another preferred embodiment, said allowing said monomeric complexes to form crystals of said nanosphere is effected at constant temperature of 4° C.-37° C., wherein said constant temperature is preferably from 10° C.-20° C. and wherein said temperature is further preferably from 16° C.-19° C.

Typically and preferably, said SEC14-like protein is obtained by heterologous expression of said SEC14-like protein in a host, wherein preferably said host is *E. coli*, and wherein optionally said heterologously expressed SEC14-like protein is purified, preferably by affinity chromatography, further preferably by affinity chromatography on Ni-NTA resin.

In again a further aspect, the present invention provides for a pharmaceutical composition comprising (a) the nanosphere of the present invention; and (b) a pharmaceutically acceptable carrier.

In another aspect, the present invention provides for the nanosphere or the pharmaceutical composition in accordance with present invention for use as a medicament.

In again a further aspect, the present invention provides for the nanosphere or the pharmaceutical composition of the present invention for use in a method of the treatment or prevention, preferably of the treatment, of Ataxia with Vitamin E Deficiency (AVED), muscle dystrophy, hypolipidemia, hypolipoproteinemia, dyslipidemia, human infertility, impaired wound healing or an inflammatory disease, wherein preferably said inflammatory disease is arthritis. Preferably said method of treatment or prevention is for a human. Further preferred is said prevention in elderly human.

In a further preferred embodiment of the present invention, said nanosphere or said pharmaceutical composition in accordance with the present invention is for use in a method of the treatment or prevention, preferably of the treatment, of Ataxia with Vitamin E Deficiency (AVED), muscle dystrophy, hypolipidemia, hypolipoproteinemia, dyslipidemia, human infertility, impaired wound healing or an inflammatory disease, wherein preferably said inflammatory disease is arthritis.

In another aspect, the present invention provides for the nanosphere or the pharmaceutical composition in accordance with present invention for use in a method of treating or preventing a disease alleviated by increasing the level of Vitamin E in a human, wherein preferably said disease is Ataxia with Vitamin E Deficiency (AVED), muscle dystrophy, hypolipidemia, hypolipoproteinemia, dyslipidemia, human infertility impaired wound healing, or an inflammatory disease, and wherein further preferably said inflammatory disease is arthritis, and wherein said human SEC14-like protein is selected from α-tocopherol transfer protein (α-TTP).

The treatment and/or prevention of wound healing in accordance with the present invention, is preferably believed to be beneficial to increase keloid formation after surgery reduce.

In another aspect, the present invention provides for the nanosphere or the pharmaceutical composition in accordance with present invention for use in a method of treating or preventing a disease alleviated by increasing the level of Vitamin A in a human, wherein preferably said disease is an eye disease or human infertility, and wherein said human SEC-14 like protein is Cellular retinaldehyde binding protein (CRALBP).

The treatment and/or prevention of human fertility in accordance with the present invention, and, thus, in particular the treatment and/or prevention of a couple's inability to conceive, is believed to be beneficial to reduce an/or eliminate the impairment of either the female uterine function or the sperm count or sperm motility.

In another aspect, the present invention provides for the use of the nanosphere or the use of the pharmaceutical composition in accordance with present invention in the manufacture of a medicament for the treatment or prevention, preferably of the treatment, of Ataxia with Vitamin E Deficiency (AVED), muscle dystrophy, hypolipidemia, hypolipoproteinemia, dyslipidemia, human infertility, impaired wound healing or an inflammatory disease, wherein preferably said inflammatory disease is arthritis.

In another aspect, the present invention provides for the use of the nanosphere or the use of the pharmaceutical composition in accordance with present invention for the treatment or prevention, preferably of the treatment, of Ataxia with Vitamin E Deficiency (AVED), muscle dystrophy, hypolipidemia, hypolipoproteinemia, dyslipidemia, human infertility, impaired wound healing or an inflammatory disease, wherein preferably said inflammatory disease is arthritis.

In another aspect, the present invention provides for a method of treatment and/or prevention, preferably of treatment, of Ataxia with Vitamin E Deficiency (AVED), muscle dystrophy, hypolipidemia, hypolipoproteinemia, dyslipidemia, human infertility, impaired wound healing or an inflammatory disease, wherein preferably said inflammatory disease is arthritis, in a human, said method comprising administering to said human an effective amount of the nanosphere or the pharmaceutical composition in accordance with present invention.

In another aspect, the present invention provides for the nanosphere or the pharmaceutical composition in accordance with present invention for use in a method of treating or preventing a disease alleviated by increasing the level of Vitamin A in a human, wherein preferably said disease is an eye disease and wherein said human SEC14-like protein is Cellular retinaldehyde binding protein (CRALBP).

In another aspect, the present invention provides for a nanosphere obtainable by any one of the inventive methods of the present invention, wherein said nanosphere comprises, preferably consists of, an equal number of: (i) a human SEC14-like protein, and (ii) a cognate ligand of said SEC14-like protein, wherein preferably said equal number is 3 to 60. In a further very preferred embodiment, said equal number is a multiple of 3, and wherein preferably said number is of 3 to 60, and wherein said human SEC14-like protein is selected from (a) α-tocopherol transfer protein (α-TTP); (b) Cellular retinaldehyde binding protein (CRALBP); (c) Clavesin1 (CLVS1); (d) Clavesin2 (CLVS2); and (e) alpha-tocopherol transfer protein like (TTPAL).

In another aspect, the present invention provides for a nanosphere obtainable by any one of the inventive methods of the present invention, wherein said nanosphere comprises, preferably consists of, an equal number of: (i) a human SEC14-like protein, and (ii) a cognate ligand of said SEC14-like protein, wherein preferably said equal number is 9 to 60. In a further very preferred embodiment, said equal number is a multiple of 3, and wherein preferably said number is of 3 to 60, and wherein said human SEC14-like protein is selected from (a) α-tocopherol transfer protein (α-TTP); (b) Cellular retinaldehyde binding protein (CRALBP); (c) Clavesin1 (CLVS1); (d) Clavesin2 (CLVS2); and (e) alpha-tocopherol transfer protein like (TTPAL).

EXAMPLES

Example 1

Expression and Purification of Monomeric α-TTP

The N-terminal (His)$_6$-tagged α-TTP expression construct was made by cloning the PCR product derived from a human cDNA library into the NdeI and XhoI sites of the pET-28a vector (Stratagene, CA. USA) using the primers 5'-GGGAATTCGCAGAGGCGC-GATCCCAG-3' (SEQ ID NO:1) and 5'-CCGTCATTGAATGCTCTCAGAAATGC-3' (SEQ ID NO:2). Protein expression was carried out in *Escherichia coli* strain BL21(DE3) under control of the T7 promoter. Transformed bacteria were grown at 37° C. to an optical density (OD$_{600}$) of 0.8 and induced with 330 mM isopropyl-thiogalactopyranoside overnight at 30° C. Bacteria were harvested by centrifuging at 7'300 g and 4° C. for 30 minutes. Bacterial pellets obtained from one liter of medium were re-suspended in 25 ml lysis buffer (20 mM Tris, pH 8.0, 100 mM NaCl, 10 mM imidazole, 0.5 (v/v) Triton X-100 and 1 mM phenylmethylsulfonyfluoride). Harvested cells were disrupted twice in a French pressure cell. The lysate was centrifuged at 39'000 g and 4° C. for 40 minutes. The clarified supernatant was passed through a column containing 12 ml of TALON Superflow (Clontech Laboratories, CA, USA). Non-specifically bound proteins were removed by rinsing the column with washing buffer (20 mM Tris, 100 mM NaCl, 10 mM imidazole, pH 8.0) until the UV absorption at 280 nm recovered the level of the base line. The protein was eluted with elution buffer (20 mM Tris, 100 mM NaCl, 150 mM imidazole, pH 8.0). The (His)$_6$-tag was cleaved off using thrombin (GE Healthcare, Little Chalfont, UK) in elution buffer (20 mM Tris, 100 mM NaCl, 150 mM imidazole, pH 8.0) at 4° C. overnight. The protein eluate was pooled and concentrated using Vivaspin (Satorius, Goettingen, DE) centrifugal concentrators (MWCO 10 kDa) to ≤2.5 mg/ml in order to prevent aggregation of apo-α-TTP.

Example 2

Preparation of Mixtures of Cognate Ligand-Complexes Composed of Monomeric α-TTP-α-Tol and of α-TTP-α-Tol Nanospheres Comprising α-TTP Trimers The formation of α-TTP-α-Tol cognate ligand-complexes was achieved by dialysing freshly prepared apo-α-TTP in the presence of detergent solubilized α-Tocopherol. In brief, a droplet of 1 mg of α-Tol was overlaid with 40.9 mg of solid sodium cholate and subsequently suspended in 1 ml of elution buffer (20 mM Tris, 100 mM NaCl, 150 mM imidazole, pH 8.0). The suspension was bath sonicated until all material had dissolved to a clear solution. Apo-α-TTP (11 ml at ≤2.5 mg/ml) was complemented with the tocopherol-sodium cholate solution at 9:1 (v/v) ratio and transferred into a CelluSep T3 dialysis tubular membrane with an MWCO range of 12-14 kDa (Membranes Filtration Products, TX, USA). Dialysis was performed in two steps against 3 l buffer (20 mM Tris, 100 mM NaCl, pH 8.0) each for six hours at 4° C. The dialysate (12 ml) was filtered through a Millex GP 0.22 µm filter (EMD Milipore, Mass., USA), supplemented with Triton X-100 at a final concentration of 0.01% (v/v), reduced to 2 ml and separated by preparative size exclusion chromatography. Fractions corresponding to the size of the monomeric α-TTP-α-Tol cognate ligand-complex were pooled and concentrated to 20 mg/ml using Vivaspin concentrators (MWCO 10 kDa; Satorius, Goettingen, DE) and directly used for crystallization. Fractions corresponding to the size of α-TTP-α-Tol nanospheres comprising α-TTP trimers were pooled and concentrated using Vivaspin concentrators (MWCO 30 kDa) to 10 mg/ml and re-purified by analytical size exclusion chromatography (SEC).

Example 3

Characterization of α-TTP-α-Tol Nanospheres Comprising α-TTP Trimers

A. Size Exclusion Chromatography

Figure 1B:
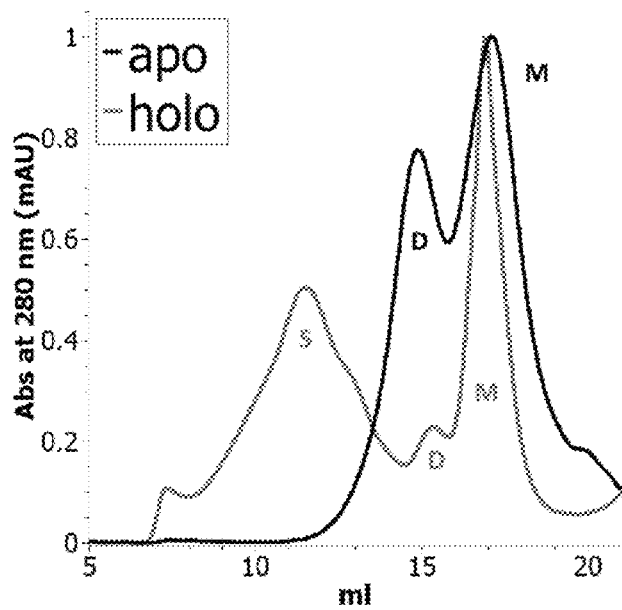

Preparative and analytical SEC of α-TTP-α-Tol nanospheres was performed on HiLoad 16/60 Supersose 75 prep grade and on Superose 6 10/300 columns respectively (GE Healthcare, Little Chalfont, UK), both attached to an AEKTA Purifier chromatography system (GE Healthcare, Little Chalfont, UK). Runs were performed in SEC buffer (10 mM Tris, 100 mM NaCl, pH 8.0) at flow rates ranging from 0.5 (analytical) to 1.5 ml/minute (preparative) at 6° C. SEC columns were calibrated using commercially available protein calibration kits (GE Healthcare, Little Chalfont, UK) (FIG. 1).

B. Negative-Stain Transmission Electron Microscopy

Figure 2:
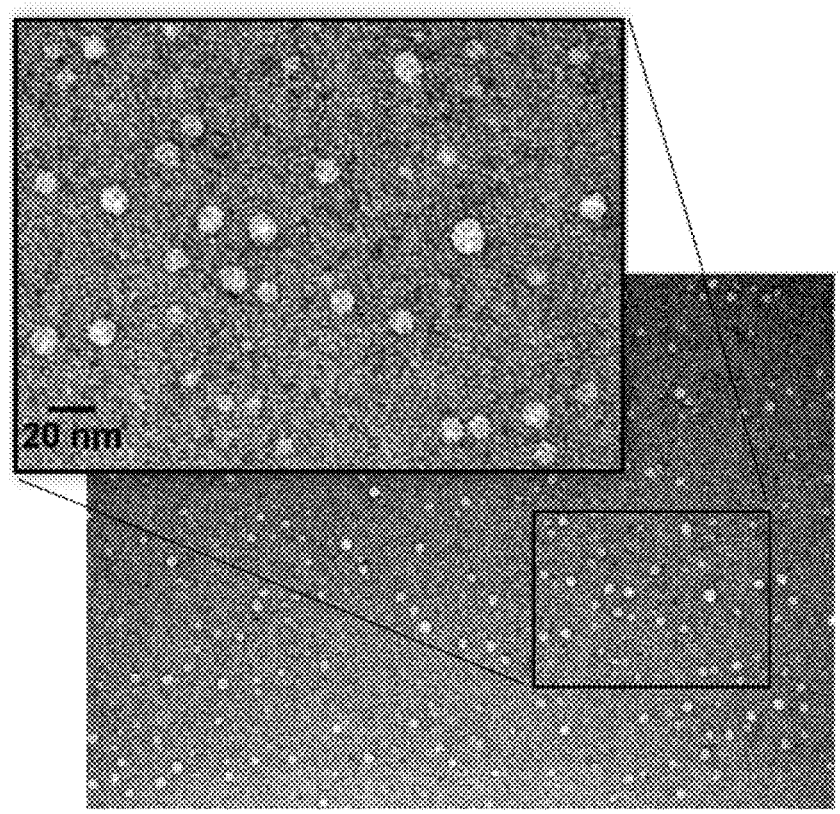
FIG. 2: Negative-stain transmission electron microscopy (TEM) images of the peak fraction of peak S from the preparative SEC revealed the physical presence of spherical objects.

A sample of α-TTP-α-Tol nanospheres at a concentration of 300 µg/ml was adsorbed for 1 minute to parlodion carbon-coated copper grids, which were previously rendered hydrophilic by glow discharge at low pressure in air. After adsorption the grids were washed with three drops of double-distilled water and stained with two drops of 0.75% uranyl formate. Electron micrographs were recorded with a Philips CM12 transmission electron microscope operated at 80 kV and equipped with a Morada CCD camera (Soft Imaging System). Image analysis was performed with the ImageJ image processing program V1.49o (NIH, MD, USA) (FIG. 2).

C. Western Blotting

Figure 3:
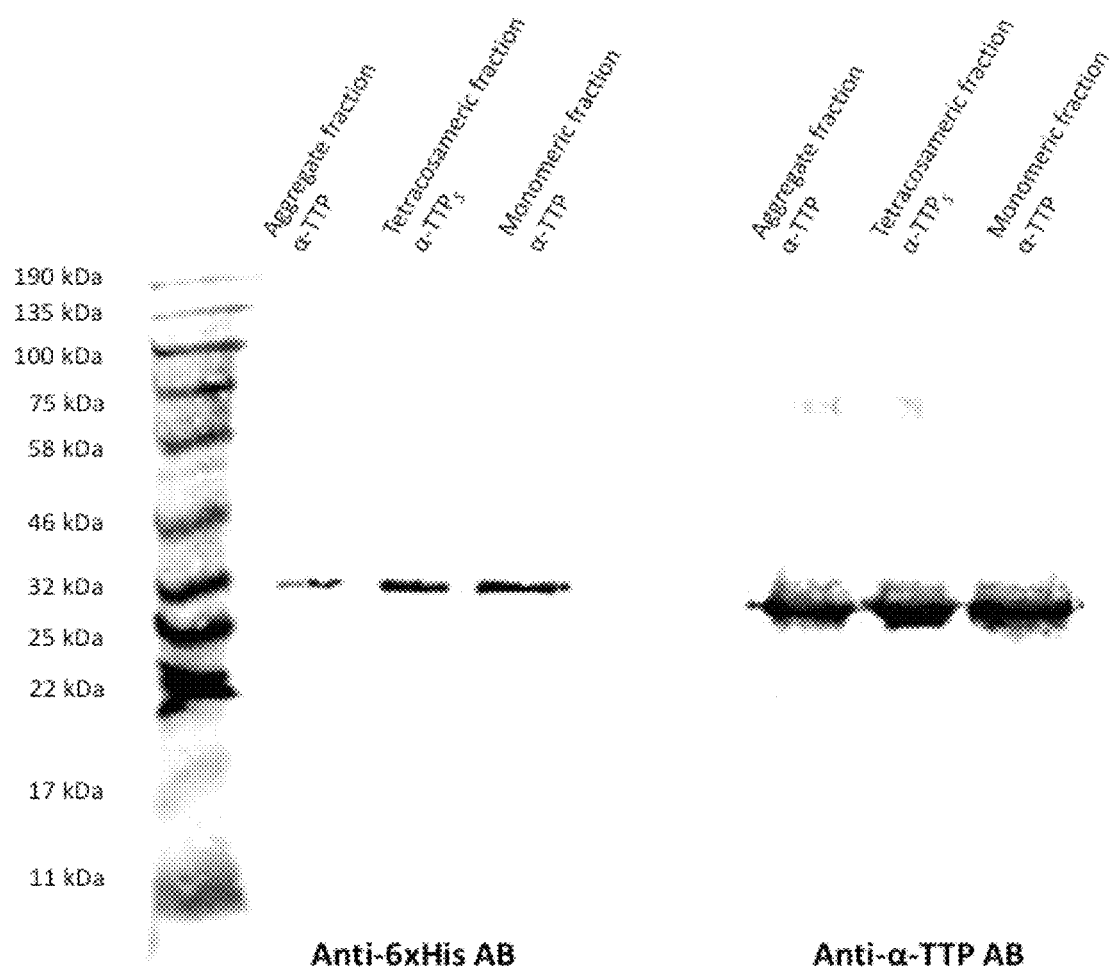
FIG. 3: Western blot of peak fractions from preparative SEC; the presence of recombinant α-TTP was confirmed by anti-6×His and by anti-α-TTP antibodies.

In brief, SDS-PAGE was carried out on 12% PAGE gels. Prior to blotting on nitrocellulose membranes gels were incubated for 20 minutes in transfer buffer (25 mM Tris, 192 mM glycine, 20% methanol, pH 8.3). Blotting was carried out at 130 mA for 50 minutes using a semi-dry blotting apparatus (Bio-Rad Laboratories, CA, USA). For analysis a commercially available primary antibody against α-TTP (alpha TTP Antibody [C2C3] C-term, GeneTex Inc., CA, USA) was used. IRDye secondary antibodies from LI-COR were employed for visualization with either IRDye 800CW or IRDye 680RD and scans were performed on a LI-COR Odyssey infrared system (LI-COR Biosystems, NE, USA) (FIG. 3).

D. Native Polyacrylamide Gel Electrophoresis

Figure 4:
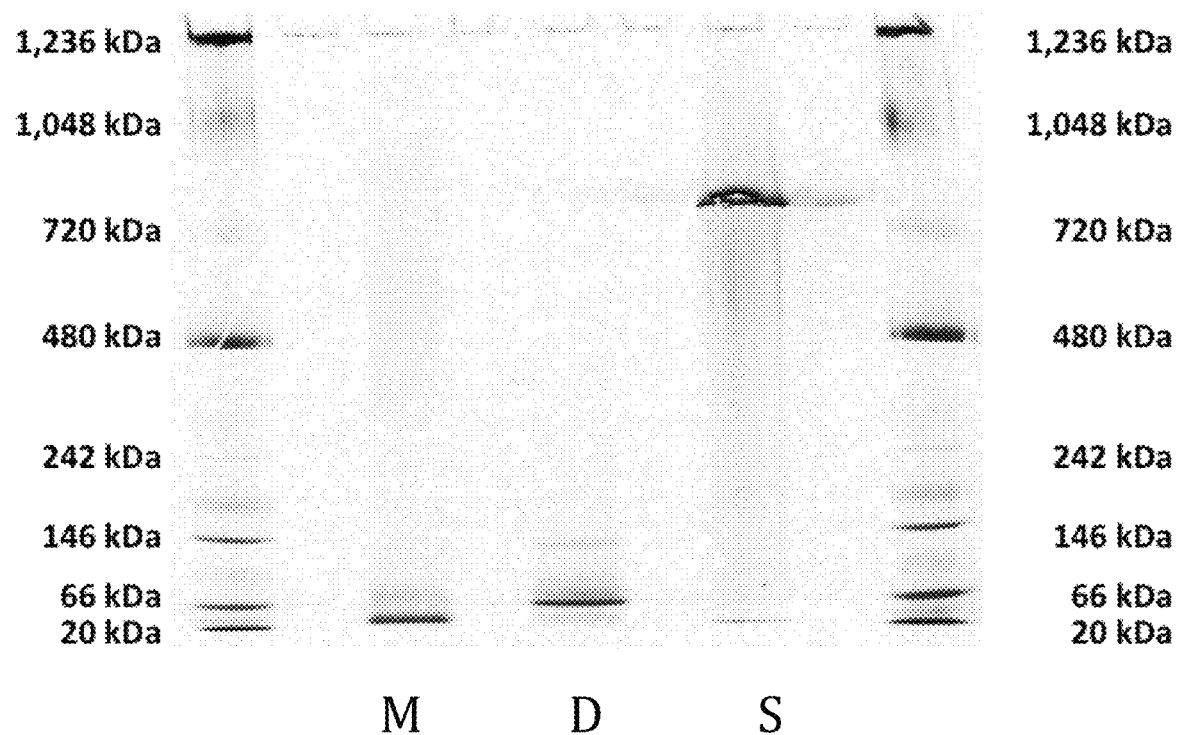
FIG. 4: Native polyacrylamide gel electrophoresis of peak fractions M, D and S from preparative SEC: Peak S contains oligomeric α-TTP-α-Tol nanospheres with an approximate mass of 0.80 MDa, peak D contains mostly homo-dimeric apo-α-TTP with an approximate mass of 64 kDa and peak M contains mostly monomeric α-TTP-α-Tol.

Native PAGE was performed using pre-cast NativePAGE Novex 4-16% Bis-Tris Protein Gels (Life Technologies, CA, USA). Each protein sample (20 µl, 0.5 mg/ml) was mixed with an equal volume of native-PAGE loading buffer (62 mM Tris, 25% glycerol, 1% bromophenol blue, pH 6.8). Gels were run at 4° C. in running buffer (50 mM Tricine, 50 mM BisTris, pH 8.0) at 160V for 30 minutes and then at 180V until the bromophenole blue marker reached the end of the gel. Protein visualization was achieved by staining with SYPRO ruby protein gel stain (Life Technologies, CA, USA) (FIG. 4).

E. Dynamic Light Scattering

Freshly pooled fractions of α-TTP-α-Tol nanospheres (concentration range 0.1-0.2 mg/ml) obtained from analytical SEC (10 mM Tris, 100 mM NaCl, pH 8.0) were analysed by dynamic light scattering (DLS). Determination of the size distribution profile of each sample was performed on a DynaPro molecular sizing instrument (Protein-Solutions) using UVettes (Eppendorf, Hamburg, DE) of 1 cm path length. Each data set was collected for at least 5 minutes containing a minimum of 100 single measurements. A hydrodynamic radius of 17.6±3.8 nm was obtained from DLS triplicate measurements.

F. Thermodynamic Analysis

Figure 5:
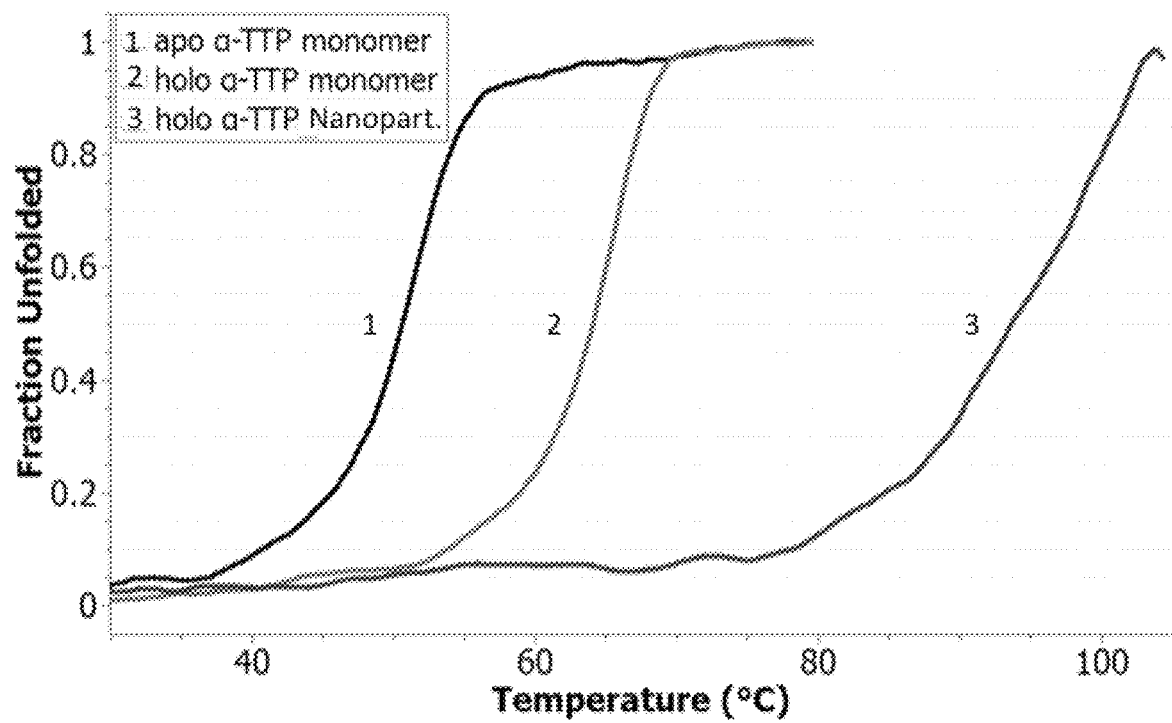
FIG. 5: Thermal denaturation traces monitored by CD spectroscopy at 222 nm for monomeric apo-α-TTP (1), monomeric α-TTP-α-Tol (2) and oligomeric α-TTP-α-Tol nanospheres (3).

A Jasco J-175 Spectropolarimeter with a Peltier PFD-350S temperature controller was used to measure CD spectra and temperature-depended protein unfolding of apo-α-TTP, monomeric α-TTP and of α-TTP-α-Tol nanospheres. For this a 1 mm path length quartz cell (with 100 µl sample) was used and the protein concentration ranged from 0.1-0.5 mg/ml. The response was set to 1 s with a bandwidth of 5 nm. Following the results from the CD spectra, the wavelength was adjusted to 222 nm for temperature-dependent protein unfolding experiments. The temperature was increased at a rate of 2 K minute$^{-1}$ from 20° C. to 80° C., for monomeric α-TTP, and from 20° C. to 100° C., for α-TTP-α-Tol nanospheres, both in increments of 0.5 K. The transition temperatures ($T_m$) were calculated from the $1^{st}$ derivative of the unfolding curves (FIG. 5).

Example 4

Crystallization and Structure Determination of α-TTP-α-Tol Nanospheres Comprising α-TTP Trimers The crystals were grown by either hanging or sitting-drop vapor diffusion using reservoir solutions ranging from 10 to 15% PEG-4000, 100-175 mM ammonium sulfate in 100 mM Hepes sodium pH 7.5 at 18° C. Freshly prepared monomeric α-TTP cognate ligand-complex was used in a concentration range between 12-22 mg/ml. Highest quality crystals of fully reduced α-TTP-α-Tol nanospheres were observed within two weeks at drop ratios of protein over reservoir ranging between 3/1 and 2/1 (v/v). Crystals had cubic shape with edge length ranging between 20 and 80 µm. Isomorphous crystals of fully oxidized α-TTP-α-Tol nanospheres were collected after two months. All crystals were flash frozen in nitrogen after adding glycerol in two steps to a final concentration of 20% (v/v). Diffraction data were collected at the Swiss Light Source (SLS) synchrotron beamline X06DA (PSI Villigen) at 100 K, employing a Dectris Pilatus 2M CCD detector (DECTRIS Ltd., Baden, Switzerland). All data were indexed, integrated and scaled with XDS (Kabsch W.; Acta Crystallographica Section D: Biological Crystallography. 2010 66:125-132). Phaser-MR was used for calculating the initial phases with the truncated structure model (residues 47-275) of monomeric α-TTP (PDB ID: 1OIP) as search structure. The atomic models of reduced α-TTP-α-Tol nanospheres and of oxidized α-TTP-α-Tol nanospheres were both refined by iterative cycles of manual model building using COOT (Emsley P, Lohkamp B, Scott W G, Cowtan K.; Acta Crystallographica Section D: Biological Crystallography. 2010 66:486-501) and restrained refinements using the Phenix programm suite (Adams P D, et al.; Acta Crystallographica Section D: Biological Crystallography. 2010 66:213-221). Coordinates and structure factors of both structures have been deposited in the RCSB Protein Data Bank with ID codes 5DI6 and 5DLU.

Example 5

Figure 6:
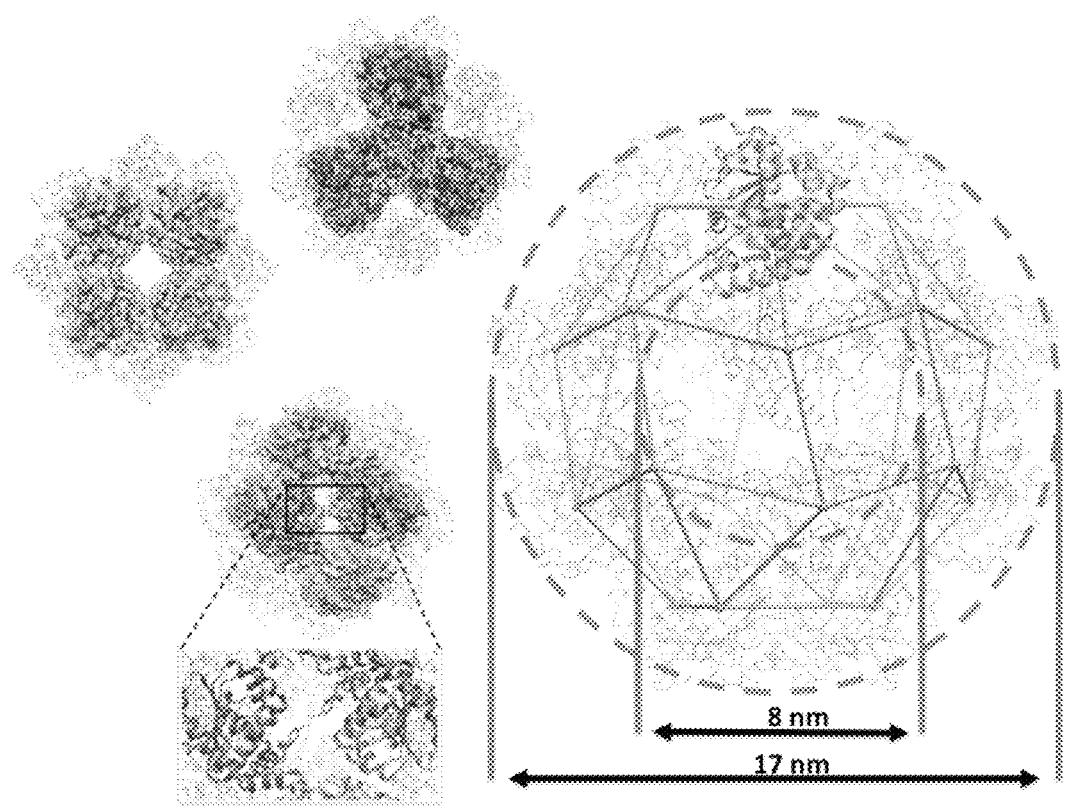
FIG. 6: Atomic model of the tetracosameric assembly of oligomeric α-TTP-α-Tol nanosphere: On the left are depicted views of the atomic model along the three symmetry axes. The inset depicts cystine bond formation between two adjacent C80 across the rhombohedral channel along the two-fold symmetry axis in the oxidized form of the α-TTP-α-Tol nanosphere. On the right is shown a geometric representation of the twisted cantellated cube (TCC) with a ribbon cartoon of a monomer sitting on a node.

Characterization of Protein-Protein Interactions Leading to the Formation of α-TTP-α-Tol Nanospheres Comprising α-TTP Trimers The α-TTP-α-Tol nanospheres crystallized exclusively when starting from monodisperse solutions of monomeric α-TTP-α-Tol cognate ligand-complex. The nanosphere comprises 24 protomers, with one α-Tol bound to each, assembled into a spheroidal shell reminiscent of a viral capsid. The X-ray structural model of α-TTP-α-Tol nanosphere, for both redox states, has an external diameter of 16.8 nm consistent in size with measurements on α-TTP-α-Tol particles from soluble preparations. The structure is further characterized by an apparently hollow cavity of 8.1 nm diameter. Closer inspection of the X-ray structural model of the particle revealed a topology of a twisted cantellated cube (point symmetry group O, Schoenflies notation) taking the centers of each protein monomer as vertexes, and connecting them through protein-protein contact interfaces. According to its point group, the nanosphere's symmetry operations are proper rotations only around three C4, four C3 and six C2 axes (FIG. 6).

Each α-TTP-α-Tol monomer is in contact with four first neighbors. With two of such neighbors, it forms one of the eight trimeric interfaces crossed by the C3 symmetry axes, and with the second two neighbors it is involved in making up one of the six tetrameric interfaces crossed by one of the C4 axes. The tetrameric unit is completed by a second neighbor unit, which is anyway not in direct contact. Twelve rhomboidal faces complete the nano cage, each crossed by one of the C2 symmetry axes. The two asymmetric edges of such interfaces correspond to those of the trimeric and tetrameric assemblies. Each monomer is involved in two of these interfaces. The oxidized from of the α-TTP-α-Tol nanosphere presents here one disulphide bridge crosslinking C80 of two α-TTP-α-Tol units through the rhombohedral channel. The oxidized α-TTP-α-Tol nanosphere thus contains at total of 12 S—S bridges covalently binding all trimeric subunits. Oxidation is accompanied by local unwinding of the helical segment (aa's 65-79). It also induces structuring of the neighbouring C-terminus (aa's 275-278) into a regular α-helical motif. No other significant structural differences are observed between the reduced and oxidized forms of α-TTP-α-Tol nanospheres.

Figures 7A, 7B:
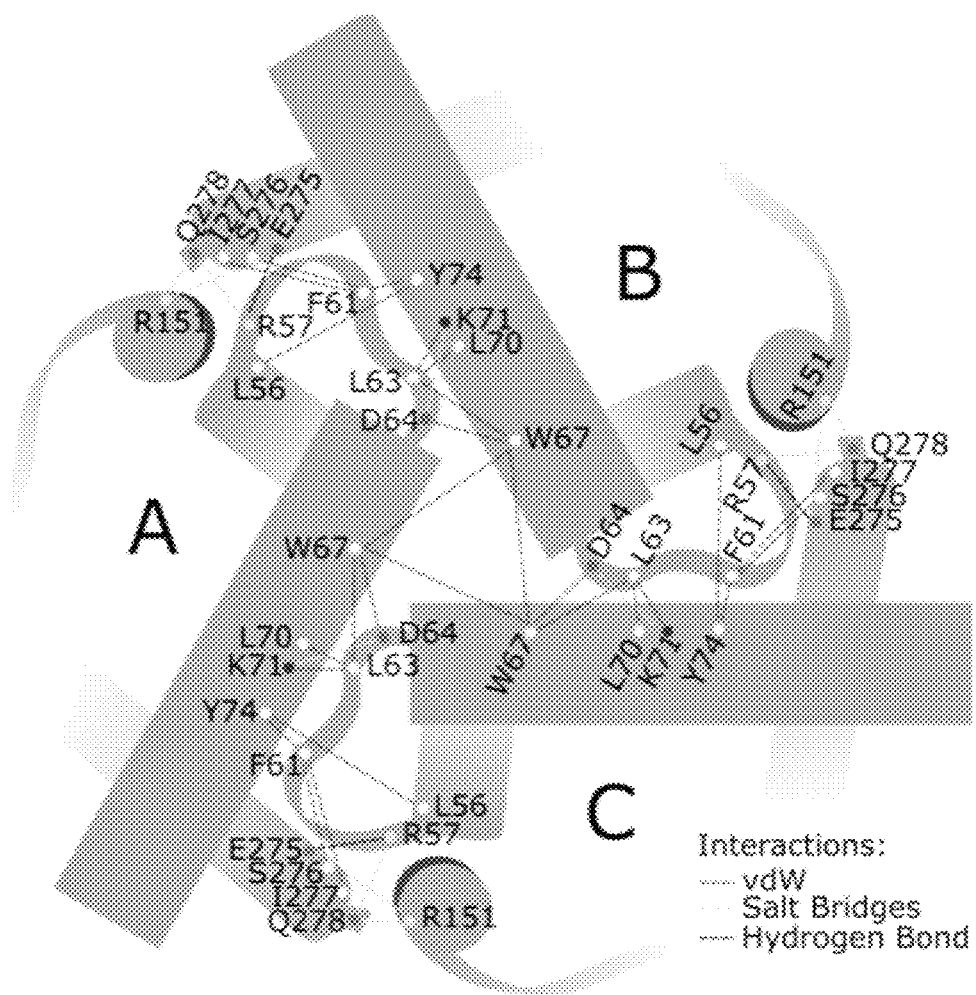
FIG. 7: A) Schematic view of protein-protein interactions on the three-fold axis (A) and summary of protein-protein interactions contributing to the stability of α-TTP-α-Tol nanospheres (B). The FoldX (Guerois R, Nielsen J E, Serrano L (2002), J Mol Bio 320:369-387) computer algorithm was used to evaluate protein-protein interactions. For this the α-TTP-α-Tol nanosphere was minimized (at 298K, pH 7, 0.05M ionic strength) in order to generate a reference structure for subsequent energy calculations and structure comparisons.

The highly packed trimeric interface is constituted by several protein-protein contacts. Each unit interacts with the following one through the helical segment 49-56, the 57-64 loop, and the first turn of the helical segment 65-79, as well as with residue R151. The partner protein interacts with the amino acids 67-74 in the helical segment 65-79, and with the C-terminal residues (aa's 275 to 278) (FIG. 7).

The trimeric interface is characterized by hydrophobic packing and further stabilized by salt bridges. These electrostatic interactions are localized mostly at the exterior of the interface, with residues R57 and R151 on one protein interacting with the C-terminus of the facing unit. Residues D64 and K71 constitute one additional salt bridge (3.87 Å, localized closer to the core of the interface. At the very center, the three W67 residues interact with each other in T-shape by van der Waals stacking. To our observation, this is the only contact point involving more than two proteins in the whole α-TTP-α-Tol nanosphere.

W67 together with L63, F61 and L56 constitute a classical "hot-spot" that accounts for roughly three quarters (77%) of the interface's overall binding free energy (Clackson T, Wells J A. Science 1995 267:383-386).

Example 6

Identification of a Conserved Sequence Pattern within the Protein-Protein Interaction Motif Leading to the Trimeric Forms of α-TTP-α-Tol Nanospheres 3-D superimposition of the α-TTP-α-Tol monomer with protomers of the α-TTP-α-Tol nanosphere evidenced that in monomeric α-TTP-α-Tol the trimeric interface is not exposed to the solvent due to folding of the N-terminal segment (aa's 1-47). Comparison of the known structures of the different members of the SEC14-like family evidenced that the N-terminal segment 1-47 was not always fully detected by X-ray scattering, indicating that this portion of the protein is less structured and more prone to refolding (Sha B1, Phillips S E, Bankaitis V A, Luo M., Nature. 1998 391:506-10; Meier R, Tomizaki T, Schulze-Briese C, Baumann U, Stocker A., J Mol Biol 2003 331: 725-734; He X, Lobsiger J, Stocker A., Proceedings of the National Academy of Sciences 2009 106:18545-18550; Christen M, et al., Journal of structural biology 2015 190:261-270). It was concluded that formation of trimeric assemblies requires unmasking of the trimerization motif by displacing the N-terminal tail of α-TTP in the outer space of the α-TTP-α-Tol nanosphere. Accordingly, the 1-47 segment was not detected in the structure on the nanosphere, probably due to conformational disorder. Analysis of the secondary structure by using the PSIPRED web service indicated that corresponding helix turn helix motifs of α-TTP (aa's 47-90) and of CRALBP (aa's 91-123) are highly similar. Within the motif a characteristic sequence pattern of mostly hydrophobic residues was determined that leads to the trimeric forms within the α-TTP-α-Tol nanospheres (FIG. 8). Primary sequence alignment of the N-terminal segment of α-TTP (aa's 47-90) with corresponding segments of related SEC14-like proteins by the Multalin webservice (Corpet, F., Nucleic Acids Res. 1988 16:10881-10890) revealed a high degree of conservation for residues within the helical segment 49-56, the 57-64 loop, and the first turn of the helical segment 65-79 (FIG. 8).

The sequences of human origin used for MULTALIN alignment were: sp|P49638|TTPA_HUMAN Alpha-tocopherol transfer protein, sp|Q9BTX7|TTPAL_HUMAN Alpha-tocopherol transfer protein-like, sp|Q8IUQ0|CLVS1_HUMAN Clavesin-1, sp|Q5SYC1|CLVS2_HUMAN Clavesin-2 and sp|P12271|RLBP1_HUMAN Retinaldehyde-binding protein 1 (FIG. 9).

Example 7

Expression and Purification of Monomeric CRALBP

Human RLBP1 cDNA was obtained from Deutsches Ressourcenzentrum für Genomforschung GmbH (JRAUp969D1020D). The N-terminal (His)$_6$-tagged CRALBP overexpression vector was constructed by cloning into the NdeI and XhoI sites of the pET-28a vector (Stratagene). The N-terminal (His)6-tagged construct was transformed into E. coli BL21 (DE3) (Invitrogen). Cells were cultured overnight with agitation at 37° C. in 120 mL LB medium containing 30 μg/mL kanamycin. The overnight culture was used to inoculate 6 L of LB medium (30 μg/mL kanamycin). The culture was grown at 20° C. to an OD600 of 0.7 and then was induced with 1 mM isopropyl-thiogalactopyranoside for 16 h. Cells were harvested by centrifugation at 5000 g for 45 min and were resuspended in 250 mL of ice-cold lysis buffer (20 mM imidazole; 100 mM NaCl; 20 mM Tris-HCl, pH 7.4; 1% wt/vol Triton X-100). The cells were disrupted by ultrasonication for 20 min, and the lysate was centrifuged at 20,000 g for 35 min to remove debris. The (His)6-tagged CRALBP was purified from the supernatant by affinity chromatography on 10 mL of Ni-NTA SUPERFLOW (Qiagen) according to the manufacturer's instructions. Briefly, the lysate was loaded on the column previously equilibrated in lysis buffer, was washed with 200 mL of lysis buffer, and was eluted in 35 mL of elution buffer (20 mM Tris-HCl, pH 7.4; 200 mM imidazole; 100 mM NaCl). Typical yields were 35-40 mg of pure CRALBP as judged by SDS/PAGE. The protein eluate was pooled and concentrated using Vivaspin (Satorius, Goettingen, DE) centrifugal concentrators (MWCO 10 kDa) to ≤10 mg/ml in order to prevent aggregation of apo-CRALBP.

Example 8

Preparation of Mixtures Composed of Cognate Ligand-Complexes of Monomeric CRALBP-11-Cis-Retinal and of CRALBP-11-Cis-Retinal Homo-Oligomers All procedures involving 11-cis-retinal were performed under dim red illumination (40-W ruby bulbs) at 4° C. unless specified. CRALBP was bound to 11-cis-retinal (1.5-fold molar excess over CRALBP) by adding the ligand at a concentration 16.7 mM in the presence of sodium cholate (55.7 mM) and incubating the mixture for 15 min at 4° C. Alternatively, CRALBP was bound to 11-cis-retinal (1.5-fold molar excess over CRALBP) by adding the ligand at a concentration 16.7 mM in ethanol and incubating the mixture for 15 min or up to 45 min at 4° C. The (His)$_6$-tag was cleaved by adding 20 units of thrombin protease (GE Healthcare) and subsequent incubation at 4° C. overnight. The protein solution was then passed through a Ni-NTA column to remove uncleaved material. The flowthrough was concentrated by Centriprep-10 (Millipore) to 20 mg/mL. Cognate ligand-complexes of CRALBP were separated on a Superose 6 SEC column (GE Healthcare).

Example 9

Figure 11A:
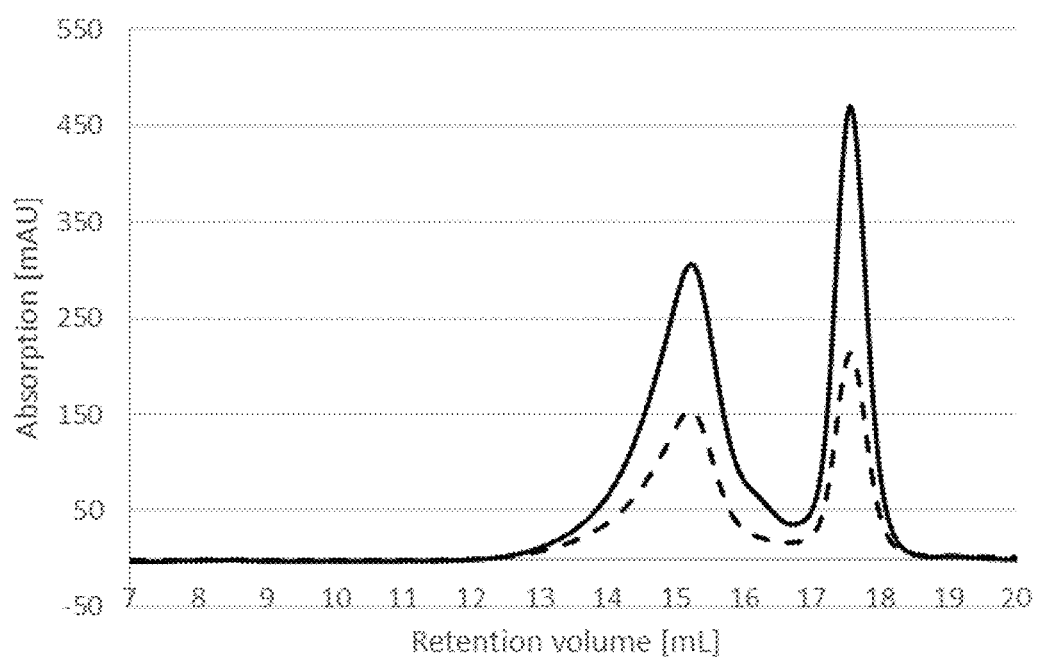
FIG. 11: Analytical SEC traces of mixtures of cognate ligand-complexes composed of monomeric CRALBP-9-cis-retinal and of CRALBP-9-cis-retinal nanospheres. A) The peak at a retention volume of 17.5 ml correlates to an average mass of 36 kDa and the peak at 15 ml correlates to an average mass of 420 kDa; B) Mixture with the ligand previously added in the presence of sodium cholate: The peak at a retention volume of 17.8 ml correlates to an average mass of 36 kDa and the peak at 13.5 ml correlates to an average mass of 1700 kDa; C) Mixture with the ligand previously added in the presence of ethanol: The peak at a retention volume of 17.8 ml correlates to an average mass of 36 kDa and the peak at 15 ml correlates to an average mass of 540 kDa. The solid traces represent the protein concentration monitored at 280 nm while the dashed traces represent the concentration of bound 9-cis-retinal monitored at 405 nm. Arrows with numbers indicate the multiplicity of the homo oligomeric complexes.
Figure 11B:
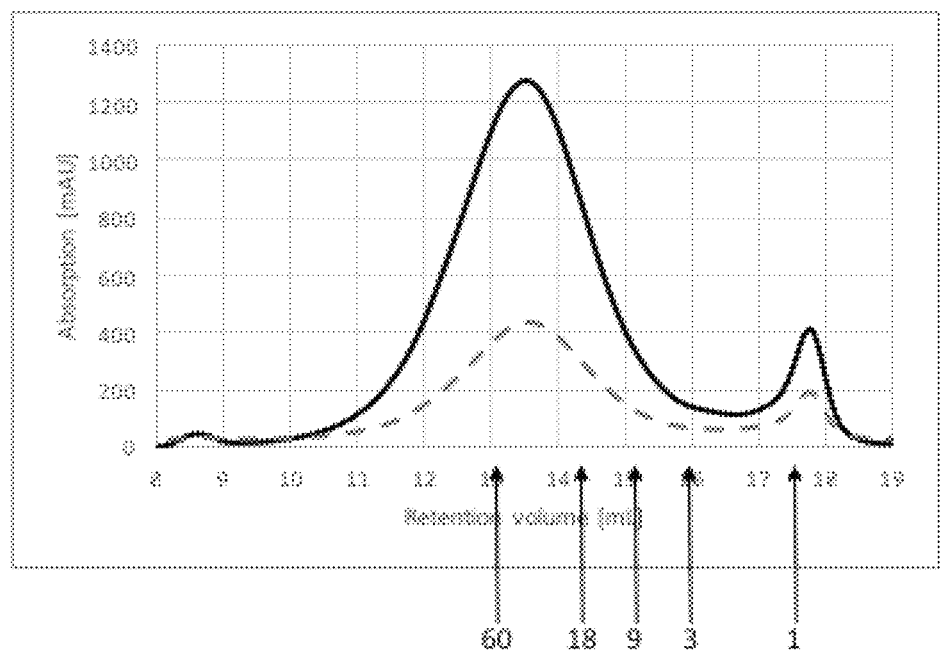
Figure 11C:
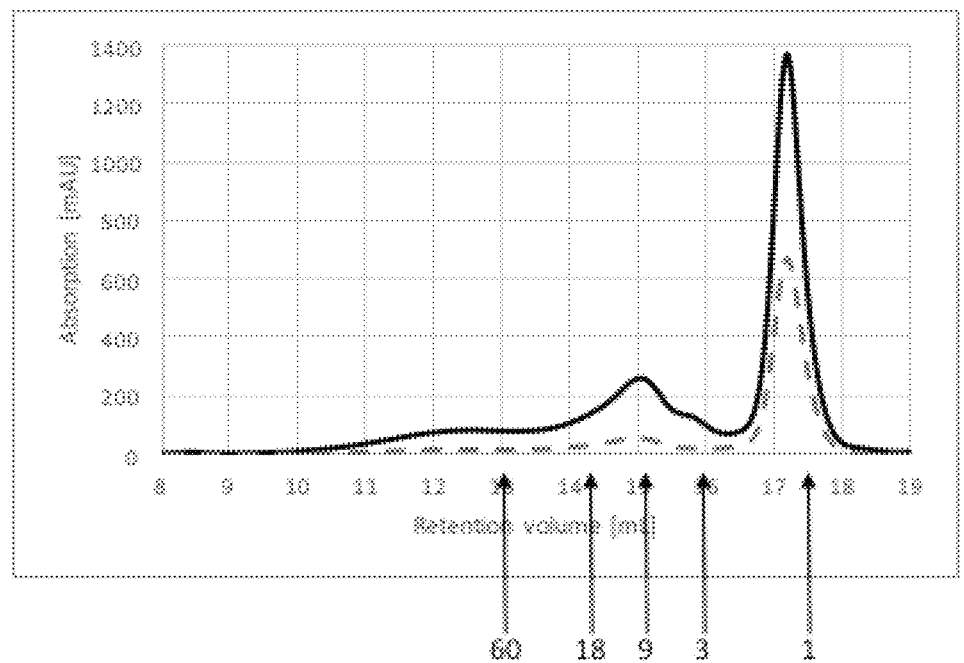

Preparation of Mixtures Composed of Cognate Ligand-Complexes of Monomeric CRALBP-9-Cis-Retinal and of CRALBP-9-Cis-Retinal Homo-Oligomers All procedures involving 9-cis-retinal were performed under dim red illumination (40-W ruby bulbs) at 4° C. unless specified. CRALBP was bound to 9-cis-retinal (1.5-fold molar excess over CRALBP) by adding the ligand at a concentration 16.7 mM in the presence of sodium cholate (55.7 mM) and incubating the mixture for 15 min at 4° C. Alternatively, CRALBP was bound to 9-cis-retinal (1.5-fold molar excess over CRALBP) by adding the ligand at a concentration 16.7 mM in ethanol and incubating the mixture for 15 min at 4° C. The (His)$_6$-tag was cleaved by 20 units of thrombin protease (GE Healthcare) at 4° C. overnight, and the protein solution was passed through a Ni-NTA column. The flowthrough was concentrated by Centriprep-10 (Millipore) to 20 mg/mL. Mixtures of cognate ligand-complexes of CRALBP were separated on a Superose 6 Increase SEC column (GE Healthcare) (FIG. 11A, FIG. 11B, FIG. 11C).

Example 10

Characterization of CRALBP-11-Cis-Retinal Homo-Oligomeric Complexes

A. Size Exclusion Chromatography
Preparative and analytical SEC of CRALBP-11-cis-retinal homo-oligomers was performed on HiLoad 16/60 Supersose 75 prep grade and on Superose 6 SEC columns respectively (GE Healthcare, Little Chalfont, UK), both attached to an AEKTA Purifier chromatography system (GE Healthcare, Little Chalfont, UK). Runs were performed in SEC buffer (20 mMTris, pH 7.4; 100 mM NaCl) at flow rates ranging from 0.5 (analytical) to 1.5 ml/minute (preparative) at 6° C. Both SEC columns were calibrated using commercially available protein calibration kits (GE Healthcare, Little Chalfont, UK). Peak fractions representing monomeric CRALBP-11-cis-retinal and homo-oligomeric CRALBP-11-cis-retinal were pooled and concentrated by Centriprep-10 (Millipore) to 20 mg/mL.

Figure 10:
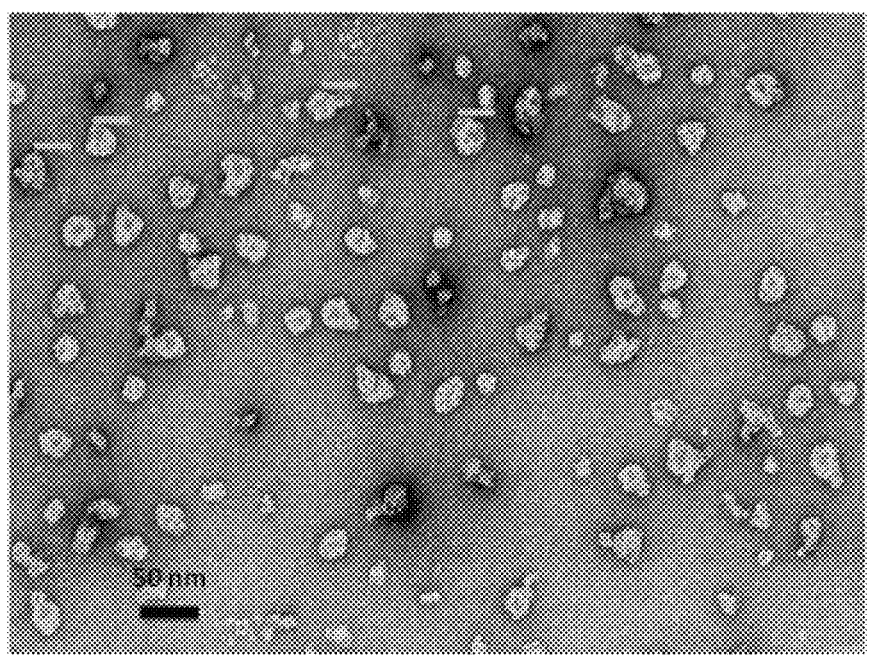
FIG. 10: Negative-stain transmission electron microscopy (TEM) images of the peak fraction of CRALBP-11-cis-retinal nanospheres from the analytical SEC revealed the physical presence of spherical objects in a size range between 9 and 48 nm.

B. Negative-Stain Transmission Electron Microscopy
A sample of CRALBP-11-cis-retinal homo-oligomers at a concentration of 0.3 mg/ml was adsorbed for 1 minute to parlodion carbon-coated copper grids, which were previously rendered hydrophilic by glow discharge at low pressure in air. After adsorption the grids were washed with three drops of double-distilled water and stained with two drops of 0.75% uranyl formate. Electron micrographs were recorded with a Philips CM12 transmission electron microscope operated at 80 kV and equipped with a Morada CCD camera (Soft Imaging System). Image analysis was performed with the ImageJ image processing program V1.490 (NIH, MD, USA) (FIG. 10).

Example 11

Characterization of CRALBP-9-Cis-Retinal Homo-Oligomeric Complexes

A. Size Exclusion Chromatography
Preparative and analytical SEC of CRALBP-9-cis-retinal homo-oligomers were performed on HiLoad 16/60 Supersose 75 prep grade and on Superose 6 Increase SEC columns respectively (GE Healthcare, Little Chalfont, UK), both attached to an AEKTA Purifier chromatography system (GE Healthcare, Little Chalfont, UK). Runs were performed in SEC buffer (20 mM Tris, pH 7.4; 100 mM NaCl) at flow rates ranging from 0.5 (analytical) to 1.5 ml/minute (preparative) at 6° C. Both SEC columns were calibrated using commercially available protein calibration kits (GE Healthcare, Little Chalfont, UK). Peak fractions representing monomeric CRALBP-9-cis-retinal and homo-oligomeric CRALBP-9-cis-retinal were pooled and concentrated by Centriprep-10 (Millipore) to 20 mg/mL (FIG. 11A, FIG. 11B, FIG. 11C).

Example 12

Figure 12A:
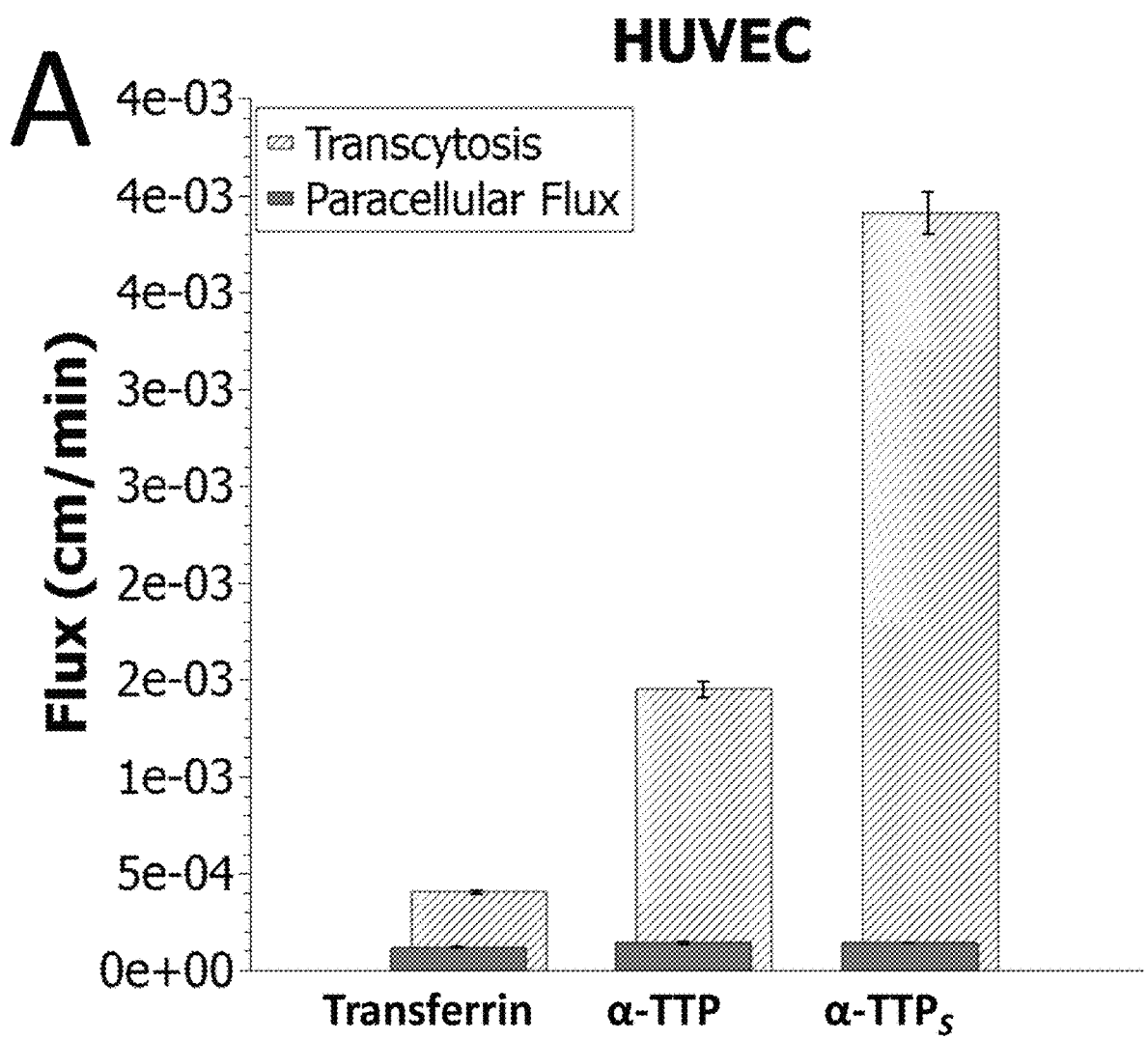
FIG. 12: Transcytosis of monomeric α-TTP-α-Tol and of α-TTP-α-Tol nanospheres comprising α-TTP trimers (A) Simultaneous determination of rates of transcytosis (hatched area) and of paracellular flux (dark area) across a human umbelical vein endothelial cell (HUVEC) monolayer. (B) Corresponding rates of transcytosis and paracellular flux across a heterogeneous human epithelial colorectal adenocarcinoma cell (CaCo-2) monolayer.
Figure 12B:
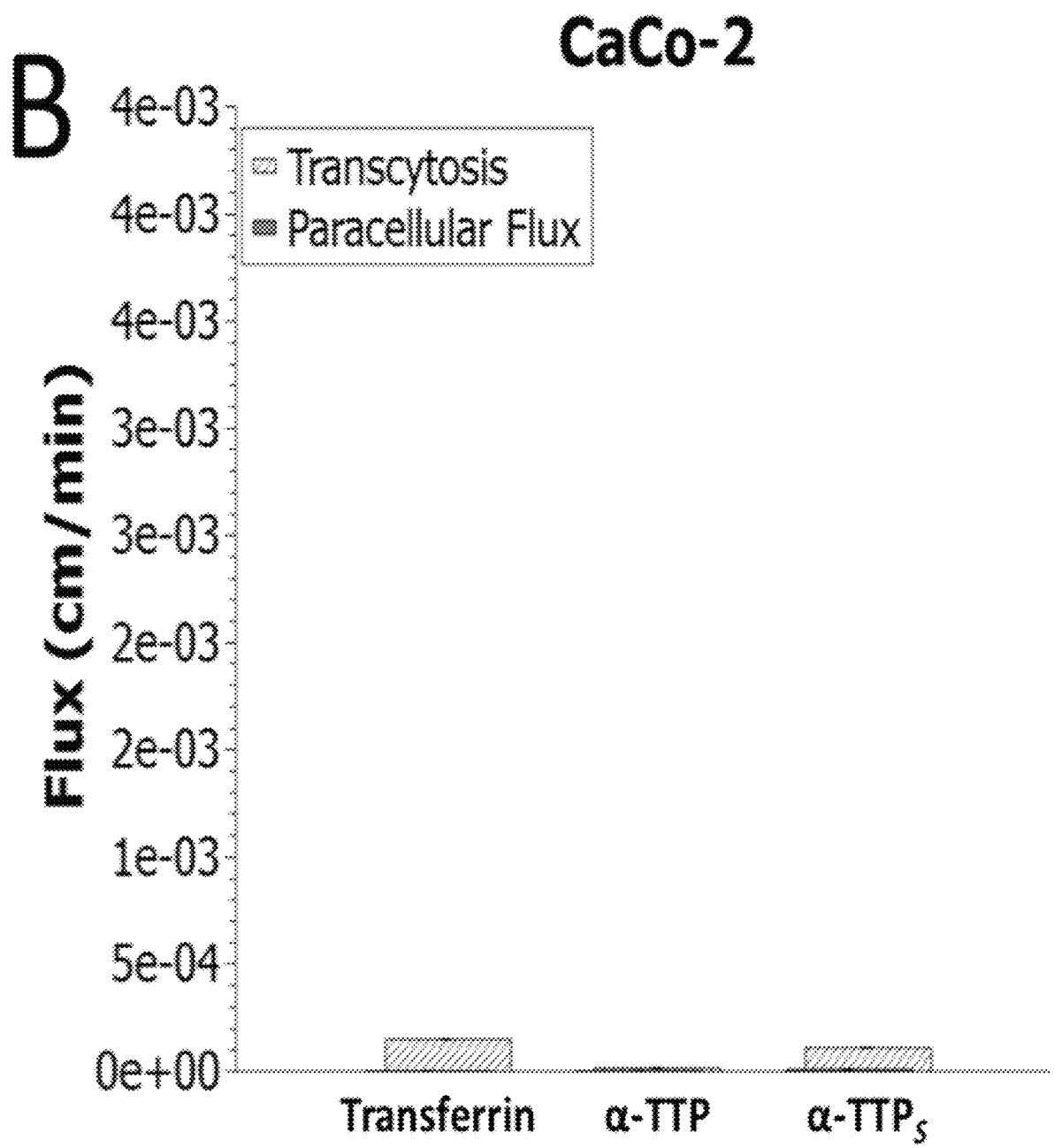

Transcytosis by α-TTP-α-Tol Nanospheres Comprising α-TTP Trimers

α-TTP fractions corresponding to monomeric and tetracosameric protein from analytic gel filtration were labeled with fluorescein isothiocyanate (FITC) according to a PIERCE method previously described by Horisberger (Horisberger, M. (1984), Polak, J., Varndel, I. Ed. Elsevier: Amsterdam, p. 98). In brief, protein samples were transferred into carbonate buffer (0.1 M, pH 9.0) for labelling using PD-10 desalting columns (GE Healthcare, Little Chalfont, UK) previously equilibrated in the same buffer. FITC was freshly dissolved before use in anhydrous DMSO (1 mg/ml). The labeling reaction was started by adding 50 µl of FITC DMSO solution to one ml of protein (1 mg/ml). The reaction mixture was incubated for 2 hours at 37° C. and stopped by removing excessive FITC using a PD-10 column previously equilibrated in PBS (10 mM phosphate, 138 mM NaCl, 27 mM KCl, pH 7.4). The labeled protein samples were finally purified by analytical SEC on a Superose 6 10/300 GL column (GE Healthcare, Little Chalfont, UK) in PBS. Transferrin was labeled by the same method and used as positive control in transcytosis experiments. In order to demonstrate promotion of transcytosis by α-TTP-α-Tol nanospheres we used endothelial primary cells from human umbelical veins (HUVECs). HUVECs were isolated from fresh umbilical cords with the help of trypsin/EDTA according to a Miltenyi Biotec protocol. Authenticity of endothelial origin was verified via positive immunofluorescence co-staining of Von Willebrand factor (vWF) and CD31. HUVECs were cultured in a Transwell system (permeable polyester membranes with 0.4 µm pore size; Corning, USA) in Endothelial Cell Growth Medium (Promocell, Germany) comprising 100 U/ml penicillin and 100 µg/ml streptomycin (PAN Biotech, Germany) with gelatine pre-coating (Sigma-Aldrich, Germany). Cells were allowed to form a tight monolayer within 7 days of culture while medium was changed every other day. For transcytosis measurements medium comprising 200 µg of RITC-dextran 70 kDa (Sigma Aldrich, MO, USA) and either 200 µg of FITC labeled monomeric α-TTP, α-TTP-α-Tol nanospheres or transferrin (as a positive control) was applied to the apical chamber, respectively. Transport was monitored by sampling 100 µl of basolateral medium at various time points (15, 30, 45, 60, 120, 180, and 240 minutes) after addition of samples to the apical chamber. Basolateral aliquots were subsequently analysed for fluorescence with a Tecan infinite200 microplate reader (Tecan, Maennedorf, CH) at an excitation wavelength of 485 nm and an emission wavelength of 535 nm (FITC) followed by measurements at an excitation wavelength of 545 nm and an emission wavelength of 590 nm (RITC), respectively. The CaCo-2/TC7 cell line (human colorectal adenocarcinoma cells; kindly provided by Dr. G. Lietz, Newcastle University, UK) representing an epithelial cell model was used as a negative control in transcytosis experiments. CaCo-2 cells were maintained in Dulbecco's Modi_ed Eagles Medium containing 4.5 g/l glucose, 4 mmol/l L-glutamine, 1 mmol/l sodium pyruvate, 100 U/ml penicillin, 100µµg/ml streptomycin (PAN Biotec, Germany) and 20% (v/v) FCS (Gibco, Germany). CaCo-2 cells are widely used as an in vivo model for barrier and transport studies (Piegholdt S, et al., Free Radical Biology and Medicine 2014 70:255-264; Kops S K, West A B, Leach J, Miller R H., The Journal of nutrition 1997 127:1744-1751; Levy E, Mehran M, Seidman E., The FASEB Journal 1995 9:626-635). CaCo-2 cells differentiate and form a tight epithelial monolayer in the same Transwell system as described above within 10 days of culture. Transcytosis experiments were performed according to the HUVEC experiments. The rate of flux was calculated as previously described by Fisher et al. (Fisher J, et al., American Journal of Physiology-Cell Physiology 2007 293:C641-C649). As a control for paracellular flux and as assurance for the formation of tight junctions, rhodamine isothiocyanate (RITC) dextran (70 kDa) was added simultaneously to the apical chamber in each experiment as tight junction control. The level of paracellular transport by RITC dextran was measured in the same manner as FITC-α-TTP, except that the RITC was detected at an excitation wavelength of 545 nm and an emission wavelength of 590 nm respectively. The different fluorescence behaviour of RITC and FITC has allowed for the simultaneous analysis of the protein of interest and the dextran control. Since dextran is not internalized at appreciable levels by endothelial cells, any accumulation of dextran in the basal chamber correlates with paracellular flux (FIG. 12).

Example 13

Transcytosis by CRALBP-Cis-Retinal Nanospheres Comprising CRALBP Trimers

CRALBP fractions corresponding to monomeric and homo oligomeric protein from analytic gel filtration is labeled with fluorescein isothiocyanate (FITC) according to a PIERCE method previously described by Horisberger (Horisberger, M. (1984)., Polak, J., Varndel, I. Ed. Elsevier: Amsterdam, p. 98). In brief, protein samples is transferred into carbonate buffer (0.1 M, pH 9.0) for labelling using PD-10 desalting columns (GE Healthcare, Little Chalfont, UK) previously equilibrated in the same buffer. FITC is freshly dissolved before use in anhydrous DMSO (1 mg/ml). The labeling reaction is started by adding 50 µl of FITC DMSO solution to one ml of protein (1 mg/ml). The reaction mixture is incubated for 2 hours at 37° C. and stopped by removing excessive FITC using a PD-10 column previously equilibrated in PBS (10 mM phosphate, 138 mM NaCl, 27 mM KCl, pH 7.4). The labeled protein samples is finally purified by analytical SEC on a Superose 6 10/300 GL column (GE Healthcare, Little Chalfont, UK) in PBS. Transferrin is labeled by the same method and used as positive control in transcytosis experiments. In order to demonstrate promotion of transcytosis by CRALBP-cis-retinal nanospheres we use endothelial primary cells from human umbelical veins (HUVECs) isolated from fresh umbilical cords with the help of trypsin/EDTA according to a Miltenyi Biotec protocol. Authenticity of endothelial origin is verified via positive immunofluorescence co-staining of Von Willebrand factor (vWF) and CD31. HUVECs is cultured in a Transwell system (permeable polyester membranes with 0.4 µm pore size; Corning, USA) in Endothelial Cell Growth Medium (Promocell, Germany) comprising 100 U/ml penicillin and 100 µg/ml streptomycin (PAN Biotech, Germany) with gelatine pre-coating (Sigma-Aldrich, Germany). Cells are allowed to form a tight monolayer within 7 days of culture while medium is changed every other day. For transcytosis measurements medium comprising 200 µg of RITC-dextran 70 kDa (Sigma Aldrich, MO, USA) and either 200 µg of FITC labeled monomeric CRALBP, CRALBP-cis-retinal nanospheres or transferrin (as a positive control) are applied to the apical chamber, respectively. Transport is monitored by sampling 100 µl of basolateral medium at various time points (15, 30, 45, 60, 120, 180, and 240 minutes) after addition of samples to the apical chamber. Basolateral aliquots are subsequently analysed for fluorescence with a Tecan infinite200 microplate reader (Tecan, Maennedorf, CH) at an excitation wavelength of 485 nm and an emission wavelength of 535 nm (FITC) followed by measurements at an excitation wavelength of 545 nm and an emission wavelength of 590 nm (RITC), respectively. The CaCo-2/TC7 cell line (human colorectal adenocarcinoma cells; kindly provided by Dr. G. Lietz, Newcastle University, UK) representing an epithelial cell model is used as a negative control in transcytosis experiments. CaCo-2 cells are maintained in Dulbecco's Modifed Eagles Medium containing 4.5 g/l glucose, 4 mmol/l L-glutamine, 1 mmol/l sodium pyruvate, 100 U/ml penicillin, 100 µg/ml streptomycin (PAN Biotec, Germany) and 20% (v/v) FCS (Gibco, Germany). CaCo-2 cells are widely used as an in vivo model for barrier and transport studies (Piegholdt S, et al., Free Radical Biology and Medicine 2014 70:255-264; Kops S K, West A B, Leach J, Miller R H., The Journal of nutrition 1997 127:1744-1751; Levy E, Mehran M, Seidman E., The FASEB Journal 1995 9:626-635). CaCo-2 cells differentiate and form a tight epithelial monolayer in the same Transwell system as described above within 10 days of culture. Transcytosis experiments are performed according to the HUVEC experiments. The rate of flux is calculated as previously described by Fisher et al. (Fisher J, et al., American Journal of Physiology-Cell Physiology 2007 293: C641-C649). As a control for paracellular flux and as assurance for the formation of tight junctions, rhodamine isothiocyanate (RITC) dextran (70 kDa) are added simultaneously to the apical chamber in each experiment as tight junction control. The level of paracellular transport by RITC dextran is measured in the same manner as FITC-ca-TTP, except that the RITC is detected at an excitation wavelength of 545 nm and an emission wavelength of 590 nm respectively. The different fluorescence behaviour of RITC and FITC allows for the simultaneous analysis of the protein of interest and the dextran control. Since dextran is not internalized at appreciable levels by endothelial cells, any accumulation of dextran in the basal chamber correlates with paracellular flux.

---

The invention claimed is:

1. A nanosphere comprising an equal number of:
   (i) a human SEC14-like protein, and
   (ii) a cognate ligand of said SEC14-like protein;
   wherein said nanosphere comprises trimers formed by said human SEC14-like protein and said cognate ligand of said SEC14-like protein, and wherein said equal number is 3 to 60.

2. The nanosphere of claim 1, wherein said human SEC14-like protein is selected from
   (a) α-tocopherol transfer protein (α-TTP);
   (b) Cellular retinaldehyde binding protein (CRALBP);
   (c) Clavesin1 (CLVS1);
   (d) Clavesin2 (CLVS2); and
   (e) alpha-tocopherol transfer protein like (TTPAL).

3. The nanosphere of claim 1, wherein said SEC14-like protein is α-tocopherol transfer protein (α-TTP).

4. The nanosphere of claim 3, wherein said cognate ligand of said α-tocopherol transfer protein (α-TTP) is a α-tocopherol.

5. The nanosphere of claim 3, wherein said cognate ligand of said α-tocopherol transfer protein (α-TTP) is R,R,R-α-tocopherol.

6. The nanosphere of claim 3, wherein said equal number is 24.

7. The nanosphere of claim 6, wherein said cognate ligand of said α-tocopherol transfer protein (α-TTP) is a α-tocopherol.

8. The nanosphere of claim 6, wherein said cognate ligand of said α-tocopherol transfer protein (α-TTP) is R,R,R-α-tocopherol.

9. The nanosphere of claim 3, wherein said cognate ligand of said α-tocopherol transfer protein (α-TTP) is a tocopherol.

10. The nanosphere of claim 1, wherein said SEC14-like protein is Cellular retinaldehyde binding protein (CRALBP).

11. The nanosphere of claim 10, wherein said cognate ligand of said CRALBP is a cis-retinol or a cis retinal.

12. The nanosphere of claim 10, wherein said cognate ligand of said CRALBP is a cis-retinol or a cis retinal, wherein said cis-retinol or said cis retinal is selected from 9-cis-retinal, 11-cis-retinal, 9,13-dicis-retinal, 9-cis-retinol, 11-cis-retinol and 9,13-dicis-retinol.

13. The nanosphere of claim 1, wherein said SEC14-like protein comprises an amino acid sequence, wherein said amino acid sequence of said SEC14-like protein comprises
(a) an amino acid residue selected from L and I on the position which corresponds to the position 56 of SEQ ID NO:3;
(b) the amino acid residue F on the position which corresponds to the position 61 of SEQ ID NO:3;
(c) an amino acid residue selected from L, V, Q, H and Y on the position which corresponds to the position 63 of SEQ ID NO:3;
(d) an amino acid residue selected from W, Y, F and L on the position which corresponds to the position 67 of SEQ ID NO:3;
(e) the amino acid residue L on the position which corresponds to the position 70 of SEQ ID NO:3; or
(f) an amino acid residue selected from Y, V, F and H on the position which corresponds to the position 74 of SEQ ID NO:3;
wherein said amino acid sequence of said SEC14-like protein comprises at least two of any one of said amino acid residues of (a)-(f).

14. A pharmaceutical composition comprising:
(a) the nanosphere of claim 1; and
(b) a pharmaceutically acceptable carrier.

15. The nanosphere of claim 1, wherein said equal number is a multiple of 3.

16. A method of producing the nanosphere of claim 1 comprising an equal number of:
(i) a human SEC14-like protein, and
(ii) a cognate ligand of said SEC14-like protein;
wherein said method comprises the steps of
(a) providing said SEC14-like protein in an aqueous solution I, wherein the concentration of said SEC14-like protein in said solution I is 1 µM to 5 mM, and wherein the pH of said solution I is 6 to 9;
(b) providing said cognate ligand of SEC14-like protein in a solution II, wherein the concentration of said cognate ligand of SEC14-like protein in said solution I is 5 µM to 500 mM, and wherein the solvent of said solution II is a water soluble solvent;
(c) generating a solution III by combining said solution I and said solution II, wherein the ratio of the concentration of said SEC14-like protein and the concentration of said cognate ligand of said SEC14-like protein in said solution III is of between 4:1 to 1:4 (molar/molar), and wherein the volume of said water soluble solvent in said solution III is of between 0.5-8% (vol/vol);
(d) allowing said SEC14-like protein and said cognate ligand of said SEC14-like protein to assemble into a nanosphere;
(e) separating said nanosphere from said solution III;
(f) optionally purifying said nanosphere.

17. A method of producing the nanosphere of claim 1 comprising an equal number of:
(i) a human SEC14-like protein, and
(ii) a cognate ligand of said SEC14-like protein;
wherein said method comprises the steps of
(a) providing said SEC14-like protein in an aqueous solution I, wherein the concentration of said SEC14-like protein in said solution I is 1 µM to 5 mM, and wherein the pH of said solution I is 6 to 9;
(b) providing said cognate ligand of SEC14-like protein in an aqueous solution II, wherein the concentration of said cognate ligand of SEC14-like protein in said solution I is 5 µM to 500 mM; and wherein said solution II comprises a detergent;
(c) generating a solution III by combining said solution I and said solution II, wherein the ratio of the concentration of said SEC14-like protein and the concentration of said cognate ligand of said SEC14-like protein in said solution III is of between 4:1 to 1:4 (molar/molar);
(d) removing said detergent from said solution III, wherein removing said detergent from said solution III allows said SEC14-like protein and said cognate ligand of said SEC14-like protein to assemble into a nanosphere;
(e) separating said nanosphere from said solution III;
(f) optionally purifying said nanosphere.

18. A method of producing the nanosphere of claim 1 comprising an equal number of:
(i) a human SEC14-like protein, and
(ii) a cognate ligand of said SEC14-like protein;
wherein said method comprises the steps of
(a) providing said SEC14-like protein in an aqueous solution I, wherein the concentration of said SEC14-like protein in said solution I is 1 µM to 5 mM, and wherein the pH of said solution I is 6 to 9;
(b) providing said cognate ligand of SEC14-like protein in a solution II, wherein the concentration of said cognate ligand of SEC14-like protein in said solution I is 5 µM to 500 mM, and wherein the solvent of said solution II is a water soluble solvent;
(c) generating a solution III by combining said solution I and said solution II, wherein the ratio of the concentration of said SEC14-like protein and the concentration of said cognate ligand of said SEC14-like protein in said solution III is of between 4:1 to 1:4 (molar/molar), and wherein the volume of said water soluble solvent in said solution III is of between 0.5-8% (vol/vol);
(d) allowing said SEC14-like protein and said cognate ligand of said SEC14-like protein to form monomeric complexes consisting of one of said SEC14-like protein and one of said cognate ligand of said SEC14-like protein;
(e) separating said monomeric complexes from said solution III;
(f) optionally purifying said monomeric complexes;
(g) generating an aqueous solution IV, wherein said solution IV comprises said monomeric complexes, and wherein the concentration of said monomeric complex in said solution IV is 5 mg/ml to 50 mg/ml; and wherein the pH of said solution IV is 6 to 9;

(h) allowing said monomeric complexes to form crystals of said nanosphere.

19. A method of producing the nanosphere of claim 1 comprising an equal number of:
  (i) a human SEC14-like protein, and
  (ii) a cognate ligand of said SEC14-like protein;
  wherein said method comprises the steps of
  (a) providing said SEC14-like protein in an aqueous solution I, wherein the concentration of said SEC14-like protein in said solution I is 1 µM to 5 mM, and wherein the pH of said solution I is 6 to 9;
  (b) providing said cognate ligand of SEC14-like protein in an aqueous solution II, wherein the concentration of said cognate ligand of SEC14-like protein in said solution I is 5 µM to 500 mM, and wherein said solution II comprises a detergent;
  (c) generating a solution III by combining said solution I and said solution II, wherein the ratio of the concentration of said SEC14-like protein and the concentration of said cognate ligand of said SEC14-like protein in said solution III is of between 4:1 to 1:4 (molar/molar);
  (d) removing said detergent from said solution III, wherein removing said detergent from said solution III allows said SEC14-like protein and said cognate ligand of said SEC14-like protein to form monomeric complexes consisting of one of said SEC14-like protein and one of said cognate ligand of said SEC14-like protein;
  (e) separating said monomeric complexes from said solution III;
  (f) optionally purifying said monomeric complexes;
  (g) generating an aqueous solution IV, wherein said solution IV comprises said monomeric complexes, and wherein the concentration of said monomeric complex in said solution IV is 5 mg/ml to 50 mg/ml, and wherein the pH of said solution IV is 6 to 9;
  (h) allowing said monomeric complexes to form crystals of said nanosphere.

* * * * *

SEQUENCE LISTING

```
<160> NUMBER OF SEQ ID NOS: 16

<210> SEQ ID NO 1
<211> LENGTH: 26
<212> TYPE: DNA
<213> ORGANISM: artificial sequence
<220> FEATURE:
<223> OTHER INFORMATION: primer

<400> SEQUENCE: 1
gggaattcgc agaggcgcga tcccag                                        26

<210> SEQ ID NO 2
<211> LENGTH: 26
<212> TYPE: DNA
<213> ORGANISM: artificial sequence
<220> FEATURE:
<223> OTHER INFORMATION: primer

<400> SEQUENCE: 2
ccgtcattga atgctctcag aaatgc                                        26

<210> SEQ ID NO 3
<211> LENGTH: 278
<212> TYPE: PRT
<213> ORGANISM: Homo sapiens

<400> SEQUENCE: 3

Met Ala Glu Ala Arg Ser Gln Pro Ser Ala Gly Pro Gln Leu Asn Ala
1               5                   10                  15

Leu Pro Asp His Ser Pro Leu Leu Gln Pro Gly Leu Ala Ala Leu Arg
                20                  25                  30

Arg Arg Ala Arg Glu Ala Gly Val Pro Leu Ala Pro Leu Pro Leu Thr
            35                  40                  45
```

```
Asp Ser Phe Leu Leu Arg Phe Leu Arg Ala Arg Asp Phe Asp Leu Asp
    50                  55                  60

Leu Ala Trp Arg Leu Leu Lys Asn Tyr Tyr Lys Trp Arg Ala Glu Cys
 65                  70                  75                  80

Pro Glu Ile Ser Ala Asp Leu His Pro Arg Ser Ile Ile Gly Leu Leu
                 85                  90                  95

Lys Ala Gly Tyr His Gly Val Leu Arg Ser Arg Asp Pro Thr Gly Ser
                100                 105                 110

Lys Val Leu Ile Tyr Arg Ile Ala His Trp Asp Pro Lys Val Phe Thr
                115                 120                 125

Ala Tyr Asp Val Phe Arg Val Ser Leu Ile Thr Ser Glu Leu Ile Val
    130                 135                 140

Gln Glu Val Glu Thr Gln Arg Asn Gly Ile Lys Ala Ile Phe Asp Leu
145                 150                 155                 160

Glu Gly Trp Gln Phe Ser His Ala Phe Gln Ile Thr Pro Ser Val Ala
                165                 170                 175

Lys Lys Ile Ala Ala Val Leu Thr Asp Ser Phe Pro Leu Lys Val Arg
                180                 185                 190

Gly Ile His Leu Ile Asn Glu Pro Val Ile Phe His Ala Val Phe Ser
                195                 200                 205

Met Ile Lys Pro Phe Leu Thr Glu Lys Ile Lys Glu Arg Ile His Met
    210                 215                 220

His Gly Asn Asn Tyr Lys Gln Ser Leu Leu Gln His Phe Pro Asp Ile
225                 230                 235                 240

Leu Pro Leu Glu Tyr Gly Gly Glu Glu Phe Ser Met Glu Asp Ile Cys
                245                 250                 255

Gln Glu Trp Thr Asn Phe Ile Met Lys Ser Glu Asp Tyr Leu Ser Ser
                260                 265                 270

Ile Ser Glu Ser Ile Gln
                275

<210> SEQ ID NO 4
<211> LENGTH: 317
<212> TYPE: PRT
<213> ORGANISM: Homo sapiens

<400> SEQUENCE: 4

Met Ser Glu Gly Val Gly Thr Phe Arg Met Val Pro Glu Glu Glu Gln
  1               5                  10                  15

Glu Leu Arg Ala Gln Leu Glu Gln Leu Thr Thr Lys Asp His Gly Pro
                 20                  25                  30

Val Phe Gly Pro Cys Ser Gln Leu Pro Arg His Thr Leu Gln Lys Ala
                 35                  40                  45

Lys Asp Glu Leu Asn Glu Arg Glu Glu Thr Arg Glu Glu Ala Val Arg
    50                  55                  60

Glu Leu Gln Glu Met Val Gln Ala Gln Ala Ser Gly Glu Glu Leu
 65                  70                  75                  80

Ala Val Ala Val Ala Glu Arg Val Gln Glu Lys Asp Ser Gly Phe Phe
                 85                  90                  95

Leu Arg Phe Ile Arg Ala Arg Lys Phe Asn Val Gly Arg Ala Tyr Glu
                100                 105                 110

Leu Leu Arg Gly Tyr Val Asn Phe Arg Leu Gln Tyr Pro Glu Leu Phe
                115                 120                 125

Asp Ser Leu Ser Pro Glu Ala Val Arg Cys Thr Ile Glu Ala Gly Tyr
    130                 135                 140
```

```
Pro Gly Val Leu Ser Ser Arg Asp Lys Tyr Gly Arg Val Val Met Leu
145                 150                 155                 160

Phe Asn Ile Glu Asn Trp Gln Ser Gln Glu Ile Thr Phe Asp Glu Ile
            165                 170                 175

Leu Gln Ala Tyr Cys Phe Ile Leu Glu Lys Leu Leu Glu Asn Glu Glu
        180                 185                 190

Thr Gln Ile Asn Gly Phe Cys Ile Ile Glu Asn Phe Lys Gly Phe Thr
            195                 200                 205

Met Gln Gln Ala Ala Ser Leu Arg Thr Ser Asp Leu Arg Lys Met Val
210                 215                 220

Asp Met Leu Gln Asp Ser Phe Pro Ala Arg Phe Lys Ala Ile His Phe
225                 230                 235                 240

Ile His Gln Pro Trp Tyr Phe Thr Thr Thr Tyr Asn Val Val Lys Pro
            245                 250                 255

Phe Leu Lys Ser Lys Leu Leu Glu Arg Val Phe Val His Gly Asp Asp
        260                 265                 270

Leu Ser Gly Phe Tyr Gln Ile Asp Glu Asn Ile Leu Pro Ser Asp
        275                 280                 285

Phe Gly Gly Thr Leu Pro Lys Tyr Asp Gly Lys Ala Val Ala Glu Gln
290                 295                 300

Leu Phe Gly Pro Gln Ala Gln Ala Glu Asn Thr Ala Phe
305                 310                 315

<210> SEQ ID NO 5
<211> LENGTH: 354
<212> TYPE: PRT
<213> ORGANISM: Homo sapiens

<400> SEQUENCE: 5

Met Gly Pro Val Ser Leu Leu Pro Lys Tyr Gln Lys Leu Asn Thr Trp
1               5                   10                  15

Asn Gly Asp Leu Ala Lys Met Thr His Leu Gln Ala Gly Leu Ser Pro
            20                  25                  30

Glu Thr Ile Glu Lys Ala Arg Leu Glu Leu Asn Glu Asn Pro Asp Val
        35                  40                  45

Leu His Gln Asp Ile Gln Gln Val Arg Asp Met Ile Ile Thr Arg Pro
    50                  55                  60

Asp Ile Gly Phe Leu Arg Thr Asp Ala Phe Ile Leu Arg Phe Leu
65                  70                  75                  80

Arg Ala Arg Lys Phe His Gln Ala Asp Ala Phe Arg Leu Leu Ala Gln
                85                  90                  95

Tyr Phe Gln Tyr Arg Gln Leu Asn Leu Asp Met Phe Lys Asn Phe Lys
            100                 105                 110

Ala Asp Asp Pro Gly Ile Lys Arg Ala Leu Ile Asp Gly Phe Pro Gly
        115                 120                 125

Val Leu Glu Asn Arg Asp His Tyr Gly Arg Lys Ile Leu Leu Leu Phe
130                 135                 140

Ala Ala Asn Trp Asp Gln Ser Arg Asn Ser Phe Thr Asp Ile Leu Arg
145                 150                 155                 160

Ala Ile Leu Leu Ser Leu Glu Val Leu Ile Glu Asp Pro Glu Leu Gln
                165                 170                 175

Ile Asn Gly Phe Ile Leu Ile Ile Asp Trp Ser Asn Phe Ser Phe Lys
            180                 185                 190

Gln Ala Ser Lys Leu Thr Pro Ser Ile Leu Lys Leu Ala Ile Glu Gly
```

```
                195                 200                 205
Leu Gln Asp Ser Phe Pro Ala Arg Phe Gly Val His Phe Val Asn
    210                 215                 220

Gln Pro Trp Tyr Ile His Ala Leu Tyr Thr Leu Ile Lys Pro Phe Leu
225                 230                 235                 240

Lys Asp Lys Thr Arg Lys Arg Ile Phe Leu His Gly Asn Asn Leu Asn
                245                 250                 255

Ser Leu His Gln Leu Ile His Pro Glu Phe Leu Pro Ser Glu Phe Gly
            260                 265                 270

Gly Thr Leu Pro Pro Tyr Asp Met Gly Thr Trp Ala Arg Thr Leu Leu
        275                 280                 285

Gly Pro Asp Tyr Ser Asp Glu Asn Asp Tyr Thr His Thr Ser Tyr Asn
    290                 295                 300

Ala Met His Val Lys His Thr Ser Ser Asn Leu Glu Arg Glu Cys Ser
305                 310                 315                 320

Pro Lys Leu Met Lys Arg Ser Gln Ser Val Val Glu Ala Gly Thr Leu
                325                 330                 335

Lys His Glu Glu Lys Gly Glu Asn Glu Asn Thr Gln Pro Leu Leu Ala
            340                 345                 350

Leu Asp

<210> SEQ ID NO 6
<211> LENGTH: 327
<212> TYPE: PRT
<213> ORGANISM: Homo sapiens

<400> SEQUENCE: 6

Met Thr His Leu Gln Ala Gly Leu Ser Pro Glu Thr Leu Glu Lys Ala
1               5                   10                  15

Arg Leu Glu Leu Asn Glu Asn Pro Asp Thr Leu His Gln Asp Ile Gln
                20                  25                  30

Glu Val Arg Asp Met Val Ile Thr Arg Pro Asp Ile Gly Phe Leu Arg
            35                  40                  45

Thr Asp Asp Ala Phe Ile Leu Arg Phe Leu Arg Ala Arg Lys Phe His
        50                  55                  60

His Phe Glu Ala Phe Arg Leu Leu Ala Gln Tyr Phe Glu Tyr Arg Gln
65                  70                  75                  80

Gln Asn Leu Asp Met Phe Lys Ser Phe Lys Ala Thr Asp Pro Gly Ile
                85                  90                  95

Lys Gln Ala Leu Lys Asp Gly Phe Pro Gly Gly Leu Ala Asn Leu Asp
            100                 105                 110

His Tyr Gly Arg Lys Ile Leu Val Leu Phe Ala Ala Asn Trp Asp Gln
        115                 120                 125

Ser Arg Tyr Thr Leu Val Asp Ile Leu Arg Ala Ile Leu Leu Ser Leu
    130                 135                 140

Glu Ala Met Ile Glu Asp Pro Glu Leu Gln Val Asn Gly Phe Val Leu
145                 150                 155                 160

Ile Ile Asp Trp Ser Asn Phe Thr Phe Lys Gln Ala Ser Lys Leu Thr
                165                 170                 175

Pro Ser Met Leu Arg Leu Ala Ile Glu Gly Leu Gln Asp Ser Phe Pro
            180                 185                 190

Ala Arg Phe Gly Gly Ile His Phe Val Asn Gln Pro Trp Tyr Ile His
        195                 200                 205

Ala Leu Tyr Thr Val Ile Arg Pro Phe Leu Lys Glu Lys Thr Arg Lys
```

```
            210                 215                 220
Arg Ile Phe Leu His Gly Asn Leu Asn Ser Leu His Gln Leu Ile
225                 230                 235                 240

His Pro Glu Ile Leu Pro Ser Glu Phe Gly Gly Met Leu Pro Tyr
                245                 250                 255

Asp Met Gly Thr Trp Ala Arg Thr Leu Leu Asp His Glu Tyr Asp Asp
            260                 265                 270

Asp Ser Glu Tyr Asn Val Asp Ser Tyr Ser Met Pro Val Lys Glu Val
                275                 280                 285

Glu Lys Glu Leu Ser Pro Lys Ser Met Lys Arg Ser Gln Ser Val Val
            290                 295                 300

Asp Pro Thr Val Leu Lys Arg Met Asp Lys Asn Glu Glu Asn Met
305                 310                 315                 320

Gln Pro Leu Leu Ser Leu Asp
                325

<210> SEQ ID NO 7
<211> LENGTH: 342
<212> TYPE: PRT
<213> ORGANISM: Homo sapiens

<400> SEQUENCE: 7

Met Ser Glu Glu Ser Asp Ser Leu Arg Thr Ser Pro Ser Val Ala Ser
1               5                   10                  15

Leu Ser Glu Asn Glu Leu Pro Pro Pro Glu Pro Gly Tyr Val
                20                  25                  30

Cys Ser Leu Thr Glu Asp Leu Val Thr Lys Ala Arg Glu Leu Gln
            35                  40                  45

Glu Lys Pro Glu Trp Arg Leu Arg Asp Val Gln Ala Leu Arg Asp Met
50                  55                  60

Val Arg Lys Glu Tyr Pro Asn Leu Ser Thr Ser Leu Asp Asp Ala Phe
65                  70                  75                  80

Leu Leu Arg Phe Leu Arg Ala Arg Lys Phe Asp Tyr Asp Arg Ala Leu
                85                  90                  95

Gln Leu Leu Val Asn Tyr His Ser Cys Arg Arg Ser Trp Pro Glu Val
                100                 105                 110

Phe Asn Asn Leu Lys Pro Ser Ala Leu Lys Asp Val Leu Ala Ser Gly
                115                 120                 125

Phe Leu Thr Val Leu Pro His Thr Asp Pro Arg Gly Cys His Val Val
                130                 135                 140

Cys Ile Arg Pro Asp Arg Trp Ile Pro Ser Asn Tyr Pro Ile Thr Glu
145                 150                 155                 160

Asn Ile Arg Ala Ile Tyr Leu Thr Leu Glu Lys Leu Ile Gln Ser Glu
                165                 170                 175

Glu Thr Gln Val Asn Gly Ile Val Ile Leu Ala Asp Tyr Lys Gly Val
                180                 185                 190

Ser Leu Ser Lys Ala Ser His Phe Gly Pro Phe Ile Ala Lys Lys Val
            195                 200                 205

Ile Gly Ile Leu Gln Asp Gly Phe Pro Ile Arg Ile Lys Ala Val His
            210                 215                 220

Val Val Asn Glu Pro Arg Ile Phe Lys Gly Ile Phe Ala Ile Ile Lys
225                 230                 235                 240

Pro Phe Leu Lys Glu Lys Ile Ala Asn Arg Phe Phe Leu His Gly Ser
                245                 250                 255
```

-continued

Asp Leu Asn Ser Leu His Thr Asn Leu Pro Arg Ser Ile Leu Pro Lys
              260                 265                 270

Glu Tyr Gly Gly Thr Ala Gly Glu Leu Asp Thr Ala Thr Trp Asn Ala
        275                 280                 285

Val Leu Leu Ala Ser Glu Asp Asp Phe Val Lys Glu Phe Cys Gln Pro
    290                 295                 300

Val Pro Ala Cys Asp Ser Ile Leu Gly Gln Thr Leu Leu Pro Glu Gly
305                 310                 315                 320

Leu Thr Ser Asp Ala Gln Cys Asp Asp Ser Leu Arg Ala Val Lys Ser
                325                 330                 335

Gln Leu Tyr Ser Cys Tyr
            340

Figures 8A, 8B, 8C:
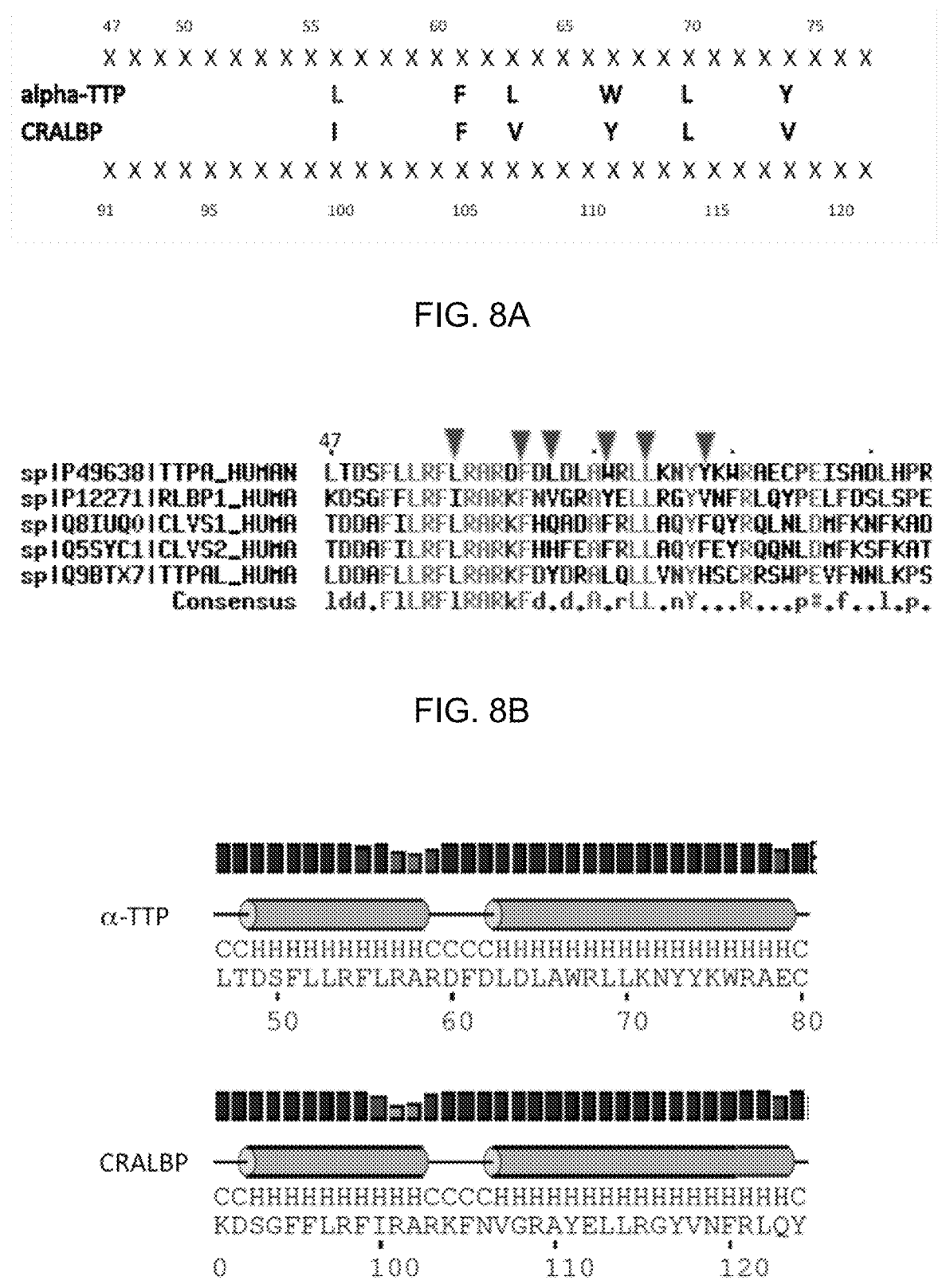

<210> SEQ ID NO 8
<211> LENGTH: 19
<212> TYPE: PRT
<213> ORGANISM: artificial sequence
<220> FEATURE:
<223> OTHER INFORMATION: FIG. 8A - alpha TTP
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(18)
<223> OTHER INFORMATION: Xaa can be any naturally occurring amino acid

<400> SEQUENCE: 8

Leu Xaa Xaa Xaa Xaa Phe Xaa Leu Xaa Xaa Xaa Trp Xaa Xaa Leu Xaa
1               5                   10                  15

Xaa Xaa Tyr

<210> SEQ ID NO 9
<211> LENGTH: 19
<212> TYPE: PRT
<213> ORGANISM: artificial sequence
<220> FEATURE:
<223> OTHER INFORMATION: Fig 8A CRALBP
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(18)

<223> OTHER INFORMATION: Xaa can be any naturally occurring amino acid

<400> SEQUENCE: 9

```
Ile Xaa Xaa Xaa Xaa Phe Xaa Val Xaa Xaa Xaa Tyr Xaa Xaa Leu Xaa
1               5                   10                  15

Xaa Xaa Val
```

<210> SEQ ID NO 10
<211> LENGTH: 44
<212> TYPE: PRT
<213> ORGANISM: artificial sequence
<220> FEATURE:
<223> OTHER INFORMATION: FIG. 8B - a-TTP aa (47-90)

<400> SEQUENCE: 10

```
Leu Thr Asp Ser Phe Leu Leu Arg Phe Leu Arg Ala Arg Asp Phe Asp
1               5                   10                  15

Leu Asp Leu Ala Trp Arg Leu Leu Lys Asn Tyr Tyr Lys Trp Arg Ala
                20                  25                  30

Glu Cys Pro Glu Ile Ser Ala Asp Leu His Pro Arg
            35                  40
```

<210> SEQ ID NO 11
<211> LENGTH: 44
<212> TYPE: PRT
<213> ORGANISM: artificial sequence
<220> FEATURE:
<223> OTHER INFORMATION: Fig. 8B - CRALBP aa (91-134)

<400> SEQUENCE: 11

```
Lys Asp Ser Gly Phe Phe Leu Arg Phe Ile Arg Ala Arg Lys Phe Asn
1               5                   10                  15

Val Gly Arg Ala Tyr Glu Leu Leu Arg Gly Tyr Val Asn Phe Arg Leu
                20                  25                  30

Gln Tyr Pro Glu Leu Phe Asp Ser Leu Ser Pro Glu
            35                  40
```

<210> SEQ ID NO 12
<211> LENGTH: 44
<212> TYPE: PRT
<213> ORGANISM: artificial sequence
<220> FEATURE:
<223> OTHER INFORMATION: Fig. 8B - CLVS1 aa (71-114)

<400> SEQUENCE: 12

```
Thr Asp Asp Ala Phe Ile Leu Arg Phe Leu Arg Ala Arg Lys Phe His
1               5                   10                  15

Gln Ala Asp Ala Phe Arg Leu Leu Ala Gln Tyr Phe Gln Tyr Arg Gln
                20                  25                  30

Leu Asn Leu Asp Met Phe Lys Asn Phe Lys Ala Asp
            35                  40
```

<210> SEQ ID NO 13
<211> LENGTH: 44
<212> TYPE: PRT
<213> ORGANISM: artificial sequence
<220> FEATURE:
<223> OTHER INFORMATION: Fig 8B - CLVS2 aa (49-92)

<400> SEQUENCE: 13

```
Thr Asp Asp Ala Phe Ile Leu Arg Phe Leu Arg Ala Arg Lys Phe His
1               5                   10                  15
```

```
His Phe Glu Ala Phe Arg Leu Leu Ala Gln Tyr Phe Glu Tyr Arg Gln
            20                  25                  30

Gln Asn Leu Asp Met Phe Lys Ser Phe Lys Ala Thr
        35                  40

<210> SEQ ID NO 14
<211> LENGTH: 44
<212> TYPE: PRT
<213> ORGANISM: artificial sequence
<220> FEATURE:
<223> OTHER INFORMATION: FIG. 8B - TTPAL aa (76-119)

<400> SEQUENCE: 14

Leu Asp Asp Ala Phe Leu Leu Arg Phe Leu Arg Ala Arg Lys Phe Asp
1               5                   10                  15

Tyr Asp Arg Ala Leu Gln Leu Leu Val Asn Tyr His Ser Cys Arg Arg
            20                  25                  30

Ser Trp Pro Glu Val Phe Asn Asn Leu Lys Pro Ser
        35                  40

<210> SEQ ID NO 15
<211> LENGTH: 34
<212> TYPE: PRT
<213> ORGANISM: artificial sequence
<220> FEATURE:
<223> OTHER INFORMATION: FIG 8C - a-TTP aa (47-80)

<400> SEQUENCE: 15

Leu Thr Asp Ser Phe Leu Leu Arg Phe Leu Arg Ala Arg Asp Phe Asp
1               5                   10                  15

Leu Asp Leu Ala Trp Arg Leu Leu Lys Asn Tyr Tyr Lys Trp Arg Ala
            20                  25                  30

Glu Cys

<210> SEQ ID NO 16
<211> LENGTH: 34
<212> TYPE: PRT
<213> ORGANISM: artificial sequence
<220> FEATURE:
<223> OTHER INFORMATION: FIG. 8C - CRALBP aa (91-124)

<400> SEQUENCE: 16

Lys Asp Ser Gly Phe Phe Leu Arg Phe Ile Arg Ala Arg Lys Phe Asn
1               5                   10                  15

Val Gly Arg Ala Tyr Glu Leu Leu Arg Gly Tyr Val Asn Phe Arg Leu
            20                  25                  30

Gln Tyr
```